(12) United States Patent
Erickson et al.

(10) Patent No.: US 10,308,943 B2
(45) Date of Patent: Jun. 4, 2019

(54) COMPOSITIONS WITH IMPROVED INTRAVITREAL HALF-LIFE AND USES THEREOF

(71) Applicant: Vitrisa Therapeutics, Inc., Larkspur, CA (US)

(72) Inventors: Carl Erickson, Corte Madera, CA (US); Christopher P. Rusconi, Durham, NC (US); Kevin G. McLure, Oakland, CA (US); Renta Hutabarat, Dracut, MA (US)

(73) Assignee: Vitrisa Therapeutics, Inc., Larkspur, CA (US)

( * ) Notice: Subject to any disclaimer, the term of this patent is extended or adjusted under 35 U.S.C. 154(b) by 0 days.

(21) Appl. No.: 15/990,542

(22) Filed: May 25, 2018

(65) Prior Publication Data

US 2018/0340179 A1  Nov. 29, 2018

Related U.S. Application Data

(63) Continuation of application No. PCT/US2017/017066, filed on Feb. 8, 2017.

(60) Provisional application No. 62/292,817, filed on Feb. 8, 2016.

(51) Int. Cl.

| A61K 45/06 | (2006.01) |
|---|---|
| C12N 15/113 | (2010.01) |
| C12N 15/115 | (2010.01) |
| A61K 9/00 | (2006.01) |
| A61K 31/7088 | (2006.01) |
| A61K 31/7105 | (2006.01) |
| A61K 31/711 | (2006.01) |
| A61K 47/54 | (2017.01) |
| A61P 27/02 | (2006.01) |

(52) U.S. Cl.
CPC .......... *C12N 15/115* (2013.01); *A61K 9/0048* (2013.01); *A61K 31/7088* (2013.01); *A61K 31/711* (2013.01); *A61K 31/7105* (2013.01); *A61K 45/06* (2013.01); *A61K 47/549* (2017.08); *A61P 27/02* (2018.01); *C07K 2317/92* (2013.01); *C07K 2317/94* (2013.01); *C12N 2310/16* (2013.01); *C12N 2310/317* (2013.01); *C12N 2310/351* (2013.01); *C12N 2310/3519* (2013.01); *C12N 2320/51* (2013.01)

(58) Field of Classification Search
CPC ............ C12N 15/1137; C12N 2310/14; C12N 2320/30; C12N 2320/35
USPC ............ 435/6.1, 91.1, 91.31, 375, 455, 458; 514/20.8, 44; 536/23.1, 24.5
See application file for complete search history.

(56) References Cited

U.S. PATENT DOCUMENTS

| 5,730,977 A | 3/1998 | Ooka et al. |
|---|---|---|
| 6,051,698 A | 4/2000 | Janjic et al. |
| 6,054,297 A | 4/2000 | Carter et al. |
| 6,344,339 B1 | 2/2002 | Menrad et al. |
| 6,403,088 B1 | 6/2002 | Alitalo et al. |
| 6,407,213 B1 | 6/2002 | Carter et al. |
| 6,573,293 B2 | 6/2003 | Tang et al. |
| 6,720,424 B1 | 4/2004 | Wada et al. |
| 6,809,097 B1 | 10/2004 | Thomas et al. |
| 6,824,777 B1 | 11/2004 | Alitalo et al. |
| 7,097,986 B2 | 8/2006 | Achen et al. |
| 7,291,601 B1 | 11/2007 | Chae et al. |
| 7,488,792 B2 | 2/2009 | Ruoslahti et al. |
| 2002/0032315 A1 | 3/2002 | Baca et al. |
| 2002/0058619 A1 | 5/2002 | Tchistiakova et al. |
| 2002/0065218 A1 | 5/2002 | Achen et al. |
| 2002/0068697 A1 | 6/2002 | Tournaire et al. |
| 2003/0088075 A1 | 5/2003 | Shitara et al. |
| 2003/0158409 A1 | 8/2003 | Bold et al. |
| 2003/0176674 A1 | 9/2003 | Rosen et al. |
| 2003/0199491 A1 | 10/2003 | Hennequin |
| 2004/0005671 A1 | 1/2004 | Nash et al. |
| 2004/0121955 A1 | 6/2004 | Mulligan-Kehoe |
| 2004/0198798 A1 | 10/2004 | Park et al. |
| 2005/0032699 A1 | 2/2005 | Holash et al. |
| 2005/0049309 A1 | 3/2005 | Kirkpatrick et al. |
| 2005/0100963 A1 | 5/2005 | Sato et al. |
| 2006/0110364 A1 | 5/2006 | Harding |
| 2006/0234941 A1 | 10/2006 | Khleif et al. |
| 2007/0027145 A1 | 2/2007 | Hennequin |
| 2007/0265286 A1 | 11/2007 | Thomas et al. |
| 2010/0254901 A1 | 10/2010 | Smith |

FOREIGN PATENT DOCUMENTS

| JP | 2002058491 A | 2/2002 |
|---|---|---|
| WO | WO-9940118 A1 | 8/1999 |
| WO | WO-02057473 A1 | 7/2002 |

(Continued)

OTHER PUBLICATIONS

Del Amo et al., European J. Pharmaceutics and Biopharmaceutics, vol. 95, Part B, pp. 215-226 (2015) (Year: 2015).*

Biesecker et al. Derivation of RNA aptamer inhibitors of human complement C5. Immunopharmacology vol. 42, Issues 1-3, May 1999, pp. 219-230.

Brockmann et al. Intravitreal inhibition of complement C5a reduces choroidal neovascularization in mice. Graefes Arch Clin Exp Ophthalmol. Oct. 2015;253(10):1695-704.

Del Amo et al. Intravitreal clearance and volume of distribution of compounds in rabbits: In silico prediction and pharmacokinetic simulations for drug development. vol. 95, Part B, Sep. 2015, pp. 215-226.

(Continued)

*Primary Examiner* — Jane J Zara
(74) *Attorney, Agent, or Firm* — Wilson Sonsini Goodrich & Rosati

(57) ABSTRACT

Provided herein are compositions and methods for the treatment of retinal diseases. The compositions and methods include a therapeutic agent conjugated to a vitreous component binding moiety. The vitreous component binding moiety may be an aptamer or a small molecule that binds to a structural component of the vitreous humor (e.g., hyaluronic acid, collagen or vitronectin).

28 Claims, 5 Drawing Sheets
Specification includes a Sequence Listing.

(56) References Cited

FOREIGN PATENT DOCUMENTS

| WO | WO-2002081520 | | 10/2002 |
|---|---|---|---|
| WO | WO-2004064760 | A2 | 8/2004 |
| WO | WO-2004087152 | A1 | 10/2004 |
| WO | WO-2007053573 | A2 | 5/2007 |
| WO | WO-2007060402 | A1 | 5/2007 |
| WO | WO-2007103549 | A2 | 9/2007 |
| WO | WO-2007140534 | A1 | 12/2007 |
| WO | WO-2008004798 | A1 | 1/2008 |
| WO | WO-2008031835 | A2 | 3/2008 |
| WO | WO-2008048079 | A1 | 4/2008 |
| WO | WO-2014099997 | A1 | 6/2014 |
| WO | WO-2015035305 | A1 | 3/2015 |
| WO | WO-2015148126 | A1 | 10/2015 |
| WO | WO-2015198243 | A2 | 12/2015 |
| WO | WO-2016073894 | A1 | 5/2016 |
| WO | WO-2017139417 | A1 | 8/2017 |
| WO | WO-2018031894 | A1 | 2/2018 |
| WO | WO-2018148333 | A1 | 8/2018 |

OTHER PUBLICATIONS

Floege et al. Novel Approach to Specific Growth Factor Inhibition in Vivo: Antagonism of Platelet-Derived Growth Factor in Glomerulonephritis by Aptamers. The American Journal of Pathology 154(1):169-179 (Jan. 1999).

Higman et al. A Refined Model for the TSG-6 Link Module in Complex with Hyaluronan—Use of Defined Oligosaccharides to Probe Structure and Function. The Journal of Biological Chemistry 289(9):5619-5634, Feb. 28, 2014.

International Search Report and Written Opinion dated May 30, 2017 for International PCT Patent Application No. PCT/US2017/017066.

Mordenti et al. Comparisons of the Intraocular Tissue Distribution, Pharmacokinetics, and Safety of 125I-Labeled Full-Length and Fab Antibodies in Rhesus Monkeys Following Intravitreal Administration. Toxicologic Pathology27(5):536-544 (1999).

Pitkänen et al. Permeability of Retinal Pigment Epithelium: Effects of Permeant Molecular Weight and Lipophilicity. Physiology and Pharmacology 46(2):641-646 (Feb. 2005).

Praidou et al. Vitreous and serum levels of vascular endothelial growth factor and platelet-derived growth factor and their correlation in patients with non-proliferative diabetic retinopathy and clinically significant macula oedema. Acta Ophthalmol. May 2011;89(3):248-54.

Ruckman et al. 2'-Fluoropyrimidine RNA-based Aptamers to the 165-Amino Acid Form of Vascular Endothelial Growth Factor (VEGF165)—Inhibition of Receptor Binding and VEGH-Induced Vascular Permeability through interactions Requiring the Exon 7-Encoded Domain. The Journal of Biological Chemistry 273(32):20556-20567 (Aug. 7, 1998).

Shatz et al. Contribution of Antibody Hydrodynamic Size to Vitreal Clearance Revealed through Rabbit Studies Using a Species-Matched Fab. Mol. Pharmaceutics, 2016, 13 (9), pp. 2996-3003.

Stuart et al. Selection of a Novel Aptamer Against Vitronectin Using Capillary Electrophoresis and Next Generation Sequencing. Mol Ther Nucleic Acids. Nov. 15, 2016;5(11):e386.

Tseng et al. Adenovirus-mediated delivery of a soluble form of the VEGF receptor Flk1 delays the growth of murine and human pancreatic adenocarcinoma in mice. Surgery 132(5):857-765 (Nov. 2002).

* cited by examiner

SEQUENCE LISTING

```
<160> NUMBER OF SEQ ID NOS: 27

<210> SEQ ID NO 1
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(63)
<223> OTHER INFORMATION: a, c, t, g, unknown or other

<400> SEQUENCE: 1
tagggaagag aaggacatat gatnnnnnnn nnnnnnnnnn nnnnnnnnnn nnnnnnnnnn      60
nnnttgacta gtacatgacc acttga                                          86

<210> SEQ ID NO 2
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
```
tagggaagag aaggacatat gattggcaag tatttgtaca tatactgacg tttgccgtac     60
tgcttgacta gtacatgacc acttga                                         86

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tggcaagtat ttgtacatat actgacgttt gccgtactgc                           40

<210> SEQ ID NO 4
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tagggaagag aaggacatat gatcacttca tgtaagacta aaagatggag cgtgaaggat     60
gcattgacta gtacatgacc acttg                                          85

<210> SEQ ID NO 5
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
cacttcatgt aagactaaaa gatggagcgt gaaggatgca                           40

<210> SEQ ID NO 6
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tagggaagag aaggacatat gattccttta gagtggcgaa gtacctaata caacctaaaa     60
tccttgacta gtacatgacc acttga                                         86

<210> SEQ ID NO 7
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tcctttagag tggcgaagta cctaatacaa cctaaaatcc                           40

<210> SEQ ID NO 8
<211> LENGTH: 9
<212> TYPE: DNA
<213> ORGANISM: Artificial Sequence
<220> FEATURE:

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 8 caggcuacg                                                                9

<210> SEQ ID NO 9
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 9
tggcaagtat ttgtacatat actgacgttt gccgtactgc                              40

<210> SEQ ID NO 10
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 10
cacttcatgt aagactaaaa gatggagcgt gaaggatgca caggcuacg                    49

<210> SEQ ID NO 11
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 11
tcctttagag tggcgaagta cctaatacaa cctaaaatcc caggcuacg                    49

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 12
cggaaucagu gaaugcuuau acauccgt                                           28

<210> SEQ ID NO 13
<211> LENGTH: 40
<212> TYPE: DNA
<213> ORGANISM: Artificial Sequence
```

<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 13
cacttcatgt aagactaaaa gatggagcgt gaaggatgca                           40

<210> SEQ ID NO 14
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 14
cgccgcgguc ucaggcgcug agucugaguu uaccugcgt                            39

<210> SEQ ID NO 15
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 15
tcctttagag tggcgaagta cctaatacaa cctaaaatcc                           40

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 16
cggaaucagu gaaugcuuau acauccgt                                       28

<210> SEQ ID NO 17
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 17
cgtagagcau ca                                                        12

<210> SEQ ID NO 18
<211> LENGTH: 9
<212> TYPE: DNA

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 18 tgatccugt                                                                9

<210> SEQ ID NO 19
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 19 caggcuacg                                                                9

<210> SEQ ID NO 20
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 20
cgtagagcau ca                                                           12

<210> SEQ ID NO 21
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 21 tgatccugt                                                                9

<210> SEQ ID NO 22
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 22
cgtagagcau ca                                                           12

<210> SEQ ID NO 23
<211> LENGTH: 9

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 23 tgatccugt                                                                  9

<210> SEQ ID NO 24
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 24
cgtagagcau ca                                                             12

<210> SEQ ID NO 25
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 25 tgatccugt                                                                  9

<210> SEQ ID NO 26
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 26
cgccgcgguc ucaggcgcug agucugaguu uaccugcgt                                39

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis Tag

<400> SEQUENCE: 27

His His His His His His
1               5
```

COMPOSITIONS WITH IMPROVED INTRAVITREAL HALF-LIFE AND USES THEREOF

CROSS-REFERENCE

This application is a continuation application of International Patent Application No. PCT/US2017/017066, filed Feb. 8, 2017, which claims the benefit of U.S. Provisional Application No. 62/292,817, filed Feb. 8, 2016, which applications are incorporated herein by reference in their entireties.

SEQUENCE LISTING

The instant application contains a Sequence Listing which has been submitted electronically in ASCII format and is hereby incorporated by reference in its entirety. Said ASCII copy, created on Feb. 7, 2017, is named 49644-704_601_SL.TXT and is 8,712 bytes in size.

BACKGROUND OF THE INVENTION

Retinal diseases and conditions affect a large population of the United States. Intravitreal (IVT) administration of retinal therapies is a common mode of administration for the treatment of retinal disease. Treatment of diseases of the posterior segment of the eye require the therapeutic to be retained in the posterior compartment of the eye (i.e. the vitreous humor) at a therapeutic concentration for a sufficient period of time to deliver a useful duration of target suppression with a tolerable dosing interval, while also being able to sufficiently diffuse to the target within the diseased-tissue to provide sufficient target occupancy to provide a therapeutic effect. For retinal diseases, a therapeutic generally must diffuse through the vitreal-retinal interface to access the intended target in the diseased tissue, and depending on the specific indication, may need to penetrate deep into retinal tissue, including reaching the retinal pigment epithelial (RPE) layer to reach the intended target at the site of disease.

Aptamers, with a compact shape and typical molecular weight ranging from 8-15 KDa, are of an ideal molecular weight for retinal penetration, but are rapidly cleared from the vitreous due to their low molecular size and weight. To increase vitreal retention, aptamers are typically conjugated to a high molecular weight PEG (e.g. 40 KDa), which due to its large hydrodynamic radius, reduces their clearance rate without greatly compromising their ability to penetrate retinal tissues. PEG does, however, greatly increase the viscosity of a drug formulation, which limits the maximum concentration of drug that can be present in a suitable formulation. Given that only a small volume is administrable by intravitreal injection, use of high molecular weight PEG limits the potential maximum dose that can be administered to the eye in a single injection.

The compositions and methods disclosed herein provide molecules exhibiting improved IVT half-lives by reducing the clearance rate, while maintaining a molecular size that allows for good retinal tissue penetration. In some examples, the compositions and methods disclosed herein provide for molecules with decreased rates of clearance from the vitreous by binding to vitreous components.

SUMMARY OF THE INVENTION

This disclosure provides oligonucleotides and other molecules that specifically bind a component of the vitreous, thereby reducing the clearance rate of these molecules and resulting in increased intravitreal residence time. The vitreous-binding oligonucleotides may be conjugated to a therapeutic agent and then may be used to ferry and dock the therapeutic agent at a vitreous component of the eye, thereby enhancing intravitreal retention of the therapeutic agent. The vitreous-binding oligonucleotides can also be formulated in a liquid solution with minimal viscosity, thereby enhancing the maximum dose deliverable to a subject by a single intravitreal injection.

In some aspects, a composition is provided comprising a therapeutic agent conjugated to a vitreous component binding moiety, wherein the vitreous component binding moiety is not a peptide tag.

In some aspects, a composition is provided comprising a therapeutic agent conjugated to a vitreous component binding moiety, wherein the vitreous component binding moiety comprises an aptamer.

In other aspects, a composition is provided comprising a therapeutic agent conjugated to a vitreous component binding moiety, wherein the vitreous component binding moiety comprises a small molecule.

In some cases, the vitreous component binding moiety of any of the foregoing compositions binds to a component of the vitreous humor. In some cases, the component of the vitreous humor is selected from the group consisting of: collagen, hyaluronan, fibrillin, vitronectin, opticin, chondroitin sulfate proteoglycan, heparan sulfate proteoglycan and any combination thereof. In one example, the component of the vitreous humor is hyaluronan. In another example, the component of the vitreous humor is collagen or collagen fibers. In yet another example, the component of the vitreous humor is vitronectin or vitronectin fibers. In some cases, the vitreous component binding moiety binds to a component of the vitreous humor with a $K_d$ of less than about 1 mM. In some cases, the vitreous component binding moiety binds to a component of the vitreous humor with a $K_d$ of less than about 100 µM. In other cases, the vitreous component binding moiety binds to a component of the vitreous humor with a $K_d$ of less than about 10 µM. In yet other cases, the vitreous component binding moiety binds to a component of the vitreous humor with a $K_d$ of less than about 1 µM. In yet other cases, the vitreous component binding moiety binds to a component of the vitreous humor with a $K_d$ of less than about 100 nM. In some cases, the composition of any of the foregoing has an intravitreal half-life of at least 6 days in a human. In some cases, the composition of any of the foregoing has an intravitreal half-life of at least 8 days in a human. In other cases, the composition of any of the foregoing has an intravitreal half-life of at least 10 days in a human. In yet other cases, the composition of any of the foregoing has an intravitreal half-life of at least 12 days in a human. In yet other cases, the composition of any of the foregoing has an intravitreal half-life of at least 14 days in a human. In some cases, the composition of any of the foregoing has an intravitreal half-life of at least 16 days in a human. In some cases, the composition of any of the foregoing has an intravitreal half-life of at least 18 days in a human. In other cases, the composition of any of the foregoing has an intravitreal half-life of at least 20 days in a human. In some cases, the therapeutic agent of any of the foregoing compositions is a therapeutic agent used for the treatment of a retinal disease. In some examples, the retinal disease is selected from the group consisting of: age-related macular degeneration, diabetic macular edema, diabetic retinopathy, retinal vein occlusion, and uveitis. In some cases, age-related macular degeneration is wet age-related macular degeneration, dry age-related macular degeneration or geographic atrophy. In some cases, the therapeutic agent of any of the foregoing compositions is an inhibitor of hypoxia-inducible factor-1α (HIF-1α), vascular endothelial growth factor (VEGF), platelet-derived growth factor (PDGF), angiopoietin-2 (Ang-2), interleukin-6 (IL-6), interleukin-2 (IL-2), interleukin-8 (IL-8), Factor D, Factor P, complement component 5 (C5), complement component 3 (C3) or integrin. In some cases, the therapeutic agent of any of the foregoing compositions is selected from the group consisting of: an aptamer, an antibody or derivative thereof, a peptide, a protein, a small molecule and any combination thereof. In some cases, the composition of any of the foregoing has a molecular weight of about 1 kDa to about 210 kDa. In some cases, the composition of any of the foregoing further comprises a polyethylene glycol (PEG) polymer. In some cases, the therapeutic agent of any of the foregoing compositions dissociates from the vitreous component binding moiety over a period of time.

In another aspect, a method is provided for treating a retinal disease in a subject, the method comprising: administering to the subject a therapeutically effective amount of a composition comprising a therapeutic agent conjugated to a vitreous component binding moiety, wherein the vitreous component binding moiety is not a peptide tag.

In another aspect, a method is provided for treating a retinal disease in a subject, the method comprising: administering to the subject a therapeutically effective amount of a composition comprising a therapeutic agent conjugated to a vitreous component binding moiety, wherein the vitreous component binding moiety is an aptamer.

In yet another aspect, a method is provided for treating a retinal disease in a subject, the method comprising: administering to the subject a therapeutically effective amount of a composition comprising a therapeutic agent conjugated to a vitreous component binding moiety, wherein the vitreous component binding moiety is a small molecule.

In some cases, the retinal disease of any of the foregoing methods is selected from the group consisting of: age-related macular degeneration, diabetic macular edema, diabetic retinopathy, retinal vein occlusion, and uveitis. In some examples, age-related macular degeneration is wet age related macular degeneration, dry age-related macular degeneration or geographic atrophy. In some cases, the administering of any of the foregoing methods comprises intravitreal administration. In some cases, the vitreous component binding moiety of any of the foregoing methods binds to a component of the vitreous humor. In some examples, the component of the vitreous humor is selected from the group consisting of: collagen, hyaluronan, fibrillin, vitronectin, opticin, chondroitin sulfate proteoglycan, heparan sulfate proteoglycan and any combination thereof. In one example, the component of the vitreous humor is hyaluronan. In another example, the component of the vitreous humor is collagen or collagen fibers. In yet another example, the component of the vitreous humor is vitronectin or vitronectin fibers. In some cases, the vitreous component binding moiety binds to a component of the vitreous humor with a $K_d$ of less than about 1 mM. In some cases, the vitreous component binding moiety binds to a component of the vitreous humor with a $K_d$ of less than about 100 μM. In other cases, the vitreous component binding moiety binds to a component of the vitreous humor with a $K_d$ of less than about 10 μM. In yet other cases, the vitreous component binding moiety binds to a component of the vitreous humor with a $K_d$ of less than about 1 μM. In yet other cases, the vitreous component binding moiety binds to a component of the vitreous humor with a $K_d$ of less than about 100 nM. In some cases, the composition of any of the foregoing methods has an intravitreal half-life of at least 6 days in a human. In some cases, the composition of any of the foregoing methods has an intravitreal half-life of at least 8 days in a human. In other cases, the composition of any of the foregoing methods has an intravitreal half-life of at least 10 days in a human. In other cases, the composition of any of the foregoing methods has an intravitreal half-life of at least 12 days in a human. In some cases, the composition of any of the foregoing methods has an intravitreal half-life of at least 14 days in a human. In some cases, the composition of any of the foregoing methods has an intravitreal half-life of at least 16 days in a human. In some cases, the composition of any of the foregoing methods has an intravitreal half-life of at least 18 days in a human. In other cases, the composition of any of the foregoing methods has an intravitreal half-life of at least 20 days in a human. In some cases, the therapeutic agent of any of the foregoing methods is an inhibitor of hypoxia-inducible factor-1α (HIF-1α), vascular endothelial growth factor (VEGF), platelet-derived growth factor (PDGF), angiopoietin-2 (Ang-2), interleukin-6 (IL-6), interleukin-2 (IL-2), interleukin-8 (IL-8), Factor D, Factor P, complement component 5 (C5), complement component 3 (C3) or integrin. In some cases, the therapeutic agent of any of the foregoing methods is selected from the group consisting of: an aptamer, an antibody or derivative thereof, a peptide, a protein, a small molecule and any combination thereof. In some cases, the composition of any of the foregoing methods is administered once every 2 weeks. In some cases, the composition of any of the foregoing methods is administered once every month. In some cases, the composition of any of the foregoing methods is administered once every 2 months. In other cases, the composition of any of the foregoing methods is administered once every 3 months. In other cases, the composition of any of the foregoing methods is administered once every 4 months. In yet other cases, the composition of any of the foregoing methods is administered once every 5 months. In yet other cases, the composition of any of the foregoing methods is administered once every 6 months. In some cases, the therapeutically effective amount of any of the foregoing methods is from about 0.1 mg to about 50 mg in about 15 μl to about 100 μl per eye. In some cases, the method of any of the foregoing further comprises co-administering at least one additional therapeutic agent to the subject. In some cases, the composition of any of the foregoing methods further comprises one or more polyethylene glycol (PEG) polymers. In some cases, the composition of any of the foregoing methods has a molecular weight of about 1 kDa to about 210 kDa. In some cases, the therapeutic agent of any of the foregoing methods dissociates from the vitreous component binding moiety over a period of time.

In another aspect, a composition is provided comprising an oligonucleotide that specifically binds to a vitreous component. In some cases, the oligonucleotide is an aptamer. The aptamer may be an RNA aptamer or a modified RNA aptamer. The aptamer may be a DNA aptamer or a modified DNA aptamer. In some instances, the aptamer comprises at least two types of nucleic acids selected from the group consisting of: DNA, modified DNA, RNA and modified RNA. In any one of the preceding compositions, the oligonucleotide may be conjugated to a therapeutic agent. In any one of the preceding compositions, the composition may be a bi-specific aptamer. In any one of the preceding compositions, the oligonucleotide may comprise a sequence according to any one of SEQ ID NOs 2-7, or comprise a sequence having at least 80% sequence identity according to any one of SEQ ID NOs 2-7. In any one of the preceding compositions, the vitreous component is hyaluronan, collagen, or vitronectin.

In yet another aspect, a composition is provided comprising a therapeutic agent conjugated to a vitreous component binding moiety, wherein the vitreous component binding moiety is not a peptide tag. The vitreous component binding moiety may bind to a component of the vitreous humor. In any one of the preceding compositions, the component of the vitreous humor may be selected from the group consisting of: collagen, hyaluronan, fibrillin, vitronectin, opticin, chondroitin sulfate proteoglycan, heparan sulfate proteoglycan and any combination thereof. In some examples, the component of the vitreous humor may be hyaluronan, collagen, or vitronectin. In any one of the preceding claims, the vitreous component binding moiety may bind to a component of the vitreous humor with a $K_d$ of less than about 1 mM. In any one of the preceding compositions, the composition may have an intravitreal half-life of at least 6 days in a human, an intravitreal half-life of at least 2 days in a rabbit, or an intravitreal half-life of at least 3 days in a non-human primate. In any one of the preceding compositions, the therapeutic agent may be a therapeutic agent used for the treatment of a retinal disease. The retinal disease may be selected from the group consisting of: wet age-related macular degeneration, dry age-related macular degeneration, geographic atrophy, diabetic macular edema, diabetic retinopathy, retinal vein occlusion, and uveitis. In any one of the preceding compositions, the therapeutic agent may be an inhibitor of hypoxia-inducible factor-1α (HIF-1α), vascular endothelial growth factor (VEGF), platelet-derived growth factor (PDGF), angiopoietin-2 (Ang-2), interleukin-6 (IL-6), interleukin-2 (IL-2), interleukin-8 (IL-8), Factor D, Factor P, complement component 5 (C5), complement component 3 (C3) or integrin. In any one of the preceding compositions, the composition may comprise an aptamer that inhibits platelet-derived growth factor (PDGF). In any one of the preceding compositions, the therapeutic agent may be selected from the group consisting of: an aptamer, an antibody or derivative thereof, a peptide, a protein, a small molecule and any combination thereof. In any one of the preceding claims the composition may have a molecular weight of about 1 kDa to about 210 kDa. In any one of the preceding claims, the composition does not comprise a polyethylene glycol (PEG) polymer of molecular weight greater than 30 kDa. In any one of the preceding compositions, the therapeutic agent may dissociate from the vitreous component binding moiety over a period of time. In any one of the preceding compositions, the vitreous component binding moiety may comprise an oligonucleotide sequence according to any one of SEQ ID NOs 2-7 or an oligonucleotide sequence having at least 80% sequence identity to any one of SEQ ID NOs 2-7. In any one of the preceding compositions, the composition may comprise an oligonucleotide sequence according to any one of SEQ ID NOs 9 and 19-21; 10, 22, and 23; 11, 24, and 25; 13 and 16; or 15 and 26; or an oligonucleotide sequence having at least 80% sequence identity to any one of SEQ ID NOs 9 and 19-21; 10, 22, and 23; 11, 24, and 25; 13 and 16; or 15 and 26. In any one of the preceding compositions, the composition may have a molecular weight of less than 40 kDa and an intravitreal retention time comparable to that of a composition comprising a 40 kDa PEG polymer. The composition may have no more than half the viscosity of the composition comprising a 40 kDa PEG polymer, when the compositions are each formulated in a liquid formulation suitable for intravitreal administration.

In another aspect, a liquid formulation is provided comprising a composition of any one of the preceding compositions, wherein the composition has a concentration in the liquid formulation of at least 40 mg/ml when formulated for intravitreal administration. In some cases, the composition has a concentration in the liquid formulation of at least 30 mg/ml, at least 40 mg/ml, at least 50 mg/ml, at least 60 mg/ml, at least 70 mg/ml, at least 80 mg/ml, at least 90 mg/ml, at least 100 mg/ml or greater when formulated for intravitreal administration. In some cases, the liquid formulation may have a dynamic viscosity of between about 38,800 centipoise to about 194,100 centipoise, about 97,000 centipoise to about 485,500 centipoise, or about 194,100 centipoise to about 970,800 centipoise when formulated in a 50 µL volume and administered with a ½ inch 27-gauge needle. In some cases, the liquid formulation may have a dynamic viscosity of between about 13,100 centipoise to about 65,000 centipoise, about 32,700 centipoise to about 164,000 centipoise, or about 65,000 centipoise to about 325,000 centipoise when formulated in a 50 µL volume and administered with a ½ inch 30-gauge needle. In some cases, the liquid formulation may have a dynamic viscosity of between about 2,800 centipoise to about 14,500 centipoise, about 7,300 centipoise to about 36,500 centipoise, or to about 14,500 to about 75,000 centipoise when formulated in a 50 µL volume and administered with a ½ inch 33-gauge needle.

In another aspect, a method is provided for treating a retinal disease in a subject, the method comprising: administering to the subject a therapeutically effective amount of a composition according to any one of the preceding compositions. The administering may comprise administering the composition to the subject by intravitreal administration. The administering of any one of the preceding methods may comprise administering the composition at least once every 8 weeks. The administering of any one of the preceding methods may comprise administering the composition using a 27-33 gauge needle. The 27-33 gauge needle may have a length of ½-inch or less. The administering of any one of the preceding methods may comprise administering a dose of the composition of at least 2 mg to the subject in a single intravitreal administration. In any one of the preceding methods, the therapeutically effective amount is from about 0.1 mg to about 50 mg in about 15 µl to about 100 µl per eye. In any one of the preceding methods, the method may further comprise co-administering at least one additional therapeutic agent to the subject.

In some embodiments, the composition of any of the foregoing has a molecular weight of less than 40 kDa. In some embodiments, the composition of any of the foregoing has a molecule weight of less than 30 kDa.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
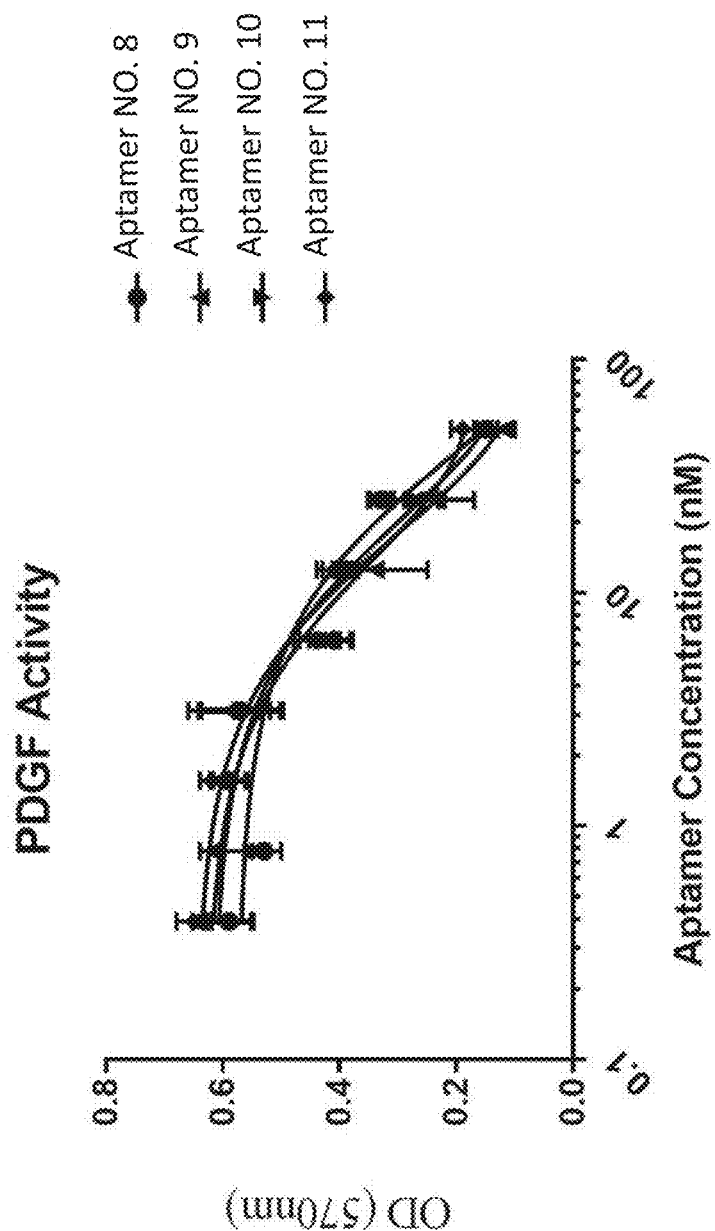
FIG. 1 depicts PDGF-dependent cell proliferation inhibition by aptamer No. 8, and by the same aptamer as part of aptamers Nos. 9, 10 and 11.
Figure 2:
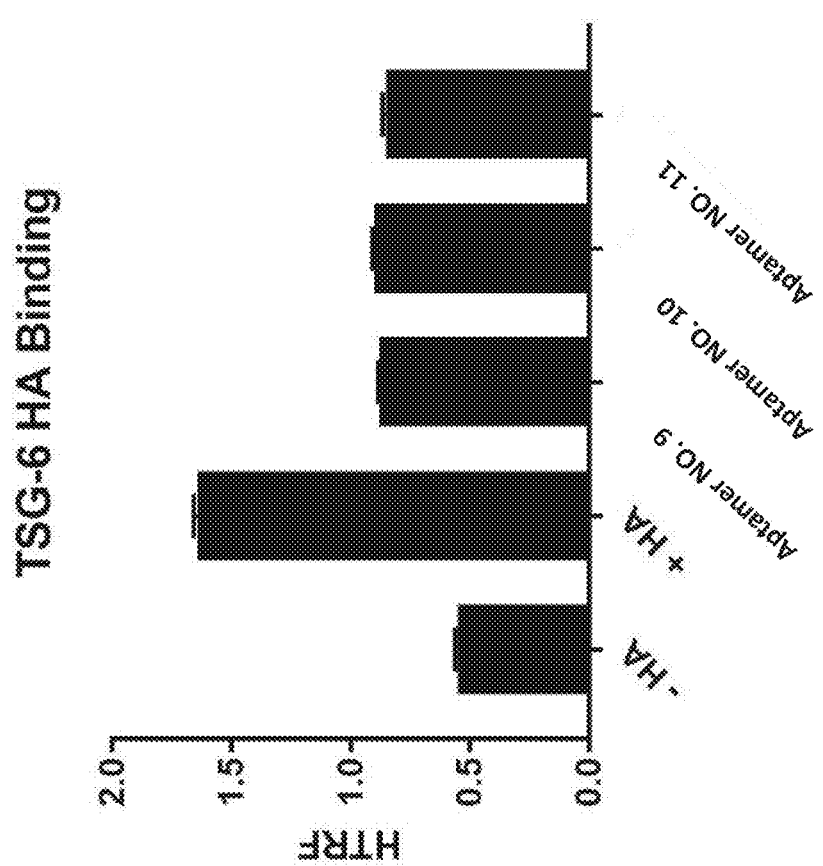
FIG. 2 depicts TSG-6 binding to HA inhibited by select aptamers.

This disclosure provides targeting oligonucleotides (e.g., aptamers) that can be used to ferry and dock therapeutic agents to compartments in the eye such as the vitreous humor. The compositions generally exhibit an improved or enhanced intravitreal (IVT) half-life due to the affinity of the oligonucleotide for a component of the vitreous. In general, the oligonucleotides provided herein easily penetrate the eye and can be provided in liquid formulations with minimal viscosity. As such, the compositions may be used to deliver therapeutically effective doses of a drug in a single administration such as a single intravitreal injection.

The compositions and methods disclosed herein may be used for the treatment of retinal diseases. The compositions may include a therapeutic agent. In some cases, the therapeutic agent is a therapeutic agent used to treat a retinal disease or disorder. The therapeutic agent can be conjugated to a vitreous component binding moiety. The vitreous component binding moiety has a binding affinity for a component of the vitreous humor, such as hyaluronan, collagen or vitronectin. Binding of the vitreous component binding moiety to a vitreous component may slow the rate of diffusion of the conjugated therapeutic agent in the vitreous, thus reducing its rate of clearance from the vitreous. In some cases, a conjugated therapeutic agent as envisioned herein has an increased intravitreal half-life relative to an unconjugated therapeutic agent.

The practice of some embodiments disclosed herein employ, unless otherwise indicated, conventional techniques of immunology, biochemistry, chemistry, molecular biology, microbiology, cell biology, genomics and recombinant DNA, which are within the skill of the art. See for example Sambrook and Green, Molecular Cloning: A Laboratory Manual, 4th Edition (2012); the series Current Protocols in Molecular Biology (F. M. Ausubel, et al. eds.); the series Methods In Enzymology (Academic Press, Inc.), PCR 2: A Practical Approach (M. J. MacPherson, B. D. Hames and G. R. Taylor eds. (1995)), Harlow and Lane, eds. (1988) Antibodies, A Laboratory Manual, and Culture of Animal Cells: A Manual of Basic Technique and Specialized Applications, 6th Edition (R. I. Freshney, ed. (2010)).

The term "aptamer" as used herein refers to an oligonucleotide and/or nucleic acid analogues that can bind to a specific target molecule. Aptamers can include RNA, DNA, RNA/DNA, any nucleic acid analogue, and/or combinations thereof. Aptamers can be single-stranded oligonucleotides. Without wishing to be bound by theory, aptamers are thought to bind to a three-dimensional structure of a target molecule. Aptamers may be monomeric (composed of a single unit) or multimeric (composed of multiple units). Multimeric aptamers can be homomeric (composed of multiple identical units) or heteromeric (composed of multiple non-identical units).

The terms "subject" and "patient" are used interchangeably herein to refer to a vertebrate, preferably a mammal, more preferably a human. Mammals include, but are not limited to, murines, simians, humans, farm animals, sport animals, and pets. Tissues, cells, and their progeny of a biological entity obtained in vivo or cultured in vitro are also encompassed.

The vitreous humor (also referred to herein as the "vitreous") is a jelly-like substance that fills the space between the lens and the retina of the eyeball of humans and other vertebrates. The vitreous humor is mostly composed of water (~98-99% of its volume) and the remainder is made up of inorganic salts, lipids, collagen fibers, hyaluronic acid, and hyalocytes (the cells that supply hyaluronic acid and collagen to the vitreous). Additional components of the vitreous humor include fibrillin, vitronectin, opticin, chondroitin sulfate proteoglycans, heparan sulfate proteoglycans, globulins, coagulation proteins, complement factors, and low-molecular-weight proteins. Unlike other fluids of the eye, such as the aqueous humor of the frontal part of the eye, the vitreous humor is stagnant and remains unchanged. Because the vitreous humor is in direct contact with the retina, intravitreal administration of therapeutic agents (i.e., administration directly to the vitreous humor) is often the choice of administration for the treatment of retinal diseases.

In some aspects of the disclosure, compositions are provided that bind to a component of the vitreous such as a vitreous component binding moiety. The component can be any component of the vitreous as described above, and in some cases, is a structural component of the vitreous. In some cases, the component is hyaluronan or hyaluronic acid. Hyaluronan is an anionic, nonsulfated glycosaminoglycan that is widely distributed throughout the vitreous. In other cases, the component is collagen. There are at least 27 different types of collagen molecules and these can assemble into fibrils or sheet-like structures. In the vitreous, nearly all of the collagen is in thin, uniform and heterotypic fibrils containing collagen types I, II, IX, and V/XI. The compositions herein then may bind to collagen fibers composed of collagen types I, II, IX, or V/XI or a combination thereof. In other cases, the component is vitronectin. Vitronectin is a highly glycosylated protein that can exist as a monomer, or a fibrillar multimer present in the vitreous. The composition herein may bind to monomeric vitronectin, of fibrils of vitronectin. In some cases, the component is fibrillin, opticin, chondroitin sulfate proteoglycans or heparan sulfate proteoglycans and the compositions bind to one or more of these components.

The terms "intravitreal half-life" or "IVT half-life" may be used interchangeably and refer to the amount of time required for the amount of a substance (e.g., a therapeutic agent) to drop to half the amount in the vitreous. For example, a therapeutic agent injected into the vitreous that falls to 50% of its injected amount in 8 days would have an IVT half-life of 8 days. The IVT half-life can be affected by a multitude of factors, non-limiting examples including stability of the agent, clearance of the agent from the vitreous, and interactions of the agent with the vitreous environment.

Contemplated herein are compositions that have an improved IVT half-life. The compositions may be therapeutic agents, in some cases therapeutic agents that are used to treat retinal diseases, that are modified or altered to improve the IVT half-life. The modifications or alterations may involve the addition of one or more vitreous component binding moieties to the therapeutic agent. The term "vitreous component binding moiety" as used herein refers to any molecule that has a binding affinity for a component of the vitreous. In some cases, the vitreous component binding moiety is an aptamer (e.g., a DNA or RNA aptamer). In some cases, the vitreous component binding moiety is a small molecule. Vitreous component binding moieties may also encompass peptides, proteins, antibodies or derivatives thereof, lipids, designed ankyrin repeat proteins (DARpins) and the like. In some cases, the vitreous component binding moiety has a binding affinity for hyaluronan (hyaluronic acid). In some cases, the vitreous component binding moiety has a binding affinity for collagen or collagen fibers. In some cases, the vitreous component binding moiety has a binding affinity for fibrillin, vitronectin, opticin, chondroitin sulfate proteoglycan or heparan sulfate proteoglycan.

Binding affinity may refer to the strength of an interaction between two binding partners, such as between a receptor and its ligand. In some cases, binding affinity may refer to the strength of an interaction between a vitreous component binding moiety and the vitreous component it binds to. Binding affinity can be represented as a dissociation constant ($K_d$), a measurement of how tightly two binding partners bind to each other, e.g., how tightly a vitreous component binding moiety (VBM) binds a vitreous component (VC). In general, a lower $K_d$ equates with tighter binding. The dissociation constant may be defined as: $K_d$=[VC][VBM]/[VC*VBM] where [VC] is the molar concentration of the vitreous component, [VBM] is the molar concentration of the vitreous component binding moiety, and [VC*VBM] is the molar concentration of the vitreous component bound by the vitreous component binding moiety. A $K_d$ value, then, is the concentration of the vitreous component binding moiety (M) at which half of the concentration of the vitreous component is bound to the vitreous component binding moiety and half of the concentration of the vitreous component is unbound.

The compositions provided herein may have $K_d$ values in the mM to μM range. Although $K_d$ values in the nM to pM range can be utilized, the balance between improving the IVT half-life of the composition and allowing the composition to eventually clear the vitreous must be considered. A composition with a $K_d$ in the pM range may bind too tightly to a vitreous component, preventing the composition from accessing the retinal surface. Therefore, in some cases, compositions with higher $K_d$ values may be utilized to overcome this. In some cases, the composition binds to a component of the vitreous with a $K_d$ of less than about 1 mM, less than about 100 μM, less than about 10 μM, less than about 1 μM, less than about 100 nM, or less than about 10 nM.

The vitreous component binding moiety can be essentially any molecule with a binding affinity for a vitreous component. In some cases, the vitreous component binding moiety is an aptamer. The term aptamer as used herein refers to oligonucleotide molecules (e.g., RNA, DNA, RNA/DNA) that bind to a target (e.g., a protein) with high affinity and specificity through non-Watson-Crick base pairing interactions. Whereas many naturally occurring oligonucleotides, such as mRNA, encode information in their linear base sequences, aptamers can be distinguished from these naturally occurring oligonucleotides in that binding of the aptamer to a target molecule is dependent upon secondary and tertiary structures of the aptamer rather than binding of a conserved linear base sequence to its complement and the aptamer generally does not encode information in its linear base sequence. Generally, the aptamers described herein are isolated, non-naturally occurring oligonucleotides (i.e., synthetically produced). When aptamers are utilized as vitreous component binding moieties, they may be designed to bind to a component of the vitreous. For example, the aptamer can bind to hyaluronan (e.g., an anti-hyaluronan aptamer). In other cases, the aptamer can bind to collagen or collagen fibers (e.g., an anti-collagen aptamer). In yet other cases, the aptamer can bind to vitronectin or vitronectin fibers.

In some instances, the vitreous component binding moiety is an aptamer that specifically binds to a vitreous component. In some cases, the vitreous component binding moiety is an aptamer that specifically binds to hyaluronan. In some examples, the vitreous component binding moiety is an aptamer comprising a sequence as described in Table 1 below.

TABLE 1

| Hyaluronan Aptamers | | | |
|---|---|---|---|
| SEQ ID NO. | Aptamer Number | Backbone | Sequence (5' to 3') |
| SEQ ID NO: 2 | Aptamer 2 | DNA | TAGGGAAGAGAAGGACATATG ATTGGCAAGTATTTGTACATAT ACTGACGTTTGCCGTACTGCTT GACTAGTACATGACCACTTGA |
| SEQ ID NO: 3 | Aptamer 3 | DNA | TGGCAAGTATTTGTACATATAC TGACGTTTGCCGTACTGC |
| SEQ ID NO: 4 | Aptamer 4 | DNA | TAGGGAAGAGAAGGACATATG ATCACTTCATGTAAGACTAAAA GATGGAGCGTGAAGGATGCAT TGACTAGTACATGACCACTTG |
| SEQ ID NO: 5 | Aptamer 5 | DNA | CACTTCATGTAAGACTAAAAG ATGGAGCGTGAAGGATGCA |

TABLE 1-continued

Hyaluronan Aptamers

| SEQ ID NO. | Aptamer Number | Backbone | Sequence (5' to 3') |
| --- | --- | --- | --- |
| SEQ ID NO: 6 | Aptamer 6 | DNA | TAGGGAAGAGAAGGACATATG<br>ATTCCTTTAGAGTGGCGAAGTA<br>CCTAATACAACCTAAAATCCTT<br>GACTAGTACATGACCACTTGA |
| SEQ ID NO: 7 | Aptamer 7 | DNA | TCCTTTAGAGTGGCGAAGTACC<br>TAATACAACCTAAAATCC |

In some cases, an aptamer of the disclosure comprises an oligonucleotide having a sequence according to any one of SEQ ID NOs 2-7 or an oligonucleotide sequence having at least 80% sequence identity of any one of SEQ ID NOs 2-7. It should be understood that where a DNA backbone has been recited, said DNA may be substituted with one or more types of nucleic acids selected from the group consisting of: modified RNA and modified DNA.

In some cases, an aptamer of the disclosure may have at least 80%, 81%, 82%, 83%, 84%, 85%, 86%, 87%, 88%, 89%, 90%, 91%, 92%, 93%, 94%, 95%, 96%, 97%, 98%, or 99% sequence identity with any aptamer described herein. For example, an aptamer of the disclosure may have at least 80%, 81%, 82%, 83%, 84%, 85%, 86%, 87%, 88%, 89%, 90%, 91%, 92%, 93%, 94%, 95%, 96%, 97%, 98%, or 99% sequence identity with any aptamer described in Table 1. In some cases, an aptamer of the disclosure may have at least 80%, 81%, 82%, 83%, 84%, 85%, 86%, 87%, 88%, 89%, 90%, 91%, 92%, 93%, 94%, 95%, 96%, 97%, 98%, or 99% sequence homology with any aptamer described herein. For example, an aptamer of the disclosure may have at least 80%, 81%, 82%, 83%, 84%, 85%, 86%, 87%, 88%, 89%, 90%, 91%, 92%, 93%, 94%, 95%, 96%, 97%, 98%, or 99% sequence homology with any aptamer described in Table 1.

In such cases where specific nucleotide modifications have been recited, it should be understood that any number and type of nucleotide modifications may be substituted. Non-limiting examples of nucleotide modifications have been provided herein. In some instances, all of the nucleotides of an aptamer of the disclosure are modified. In some instances, at least 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% of the nucleotides of an aptamer of the disclosure may be modified.

In some cases, the vitreous component binding moiety is a small molecule. In some cases, the small molecule can bind to hyaluronan. In other cases, the small molecule can bind to collagen or collagen fibers. Non-limiting examples of such molecules include: any of those described in U.S. Pat. No. 7,488,792; and galloyl-containing compounds such as tannic acid, epigallocatechin gallate, epicatechin gallate, and gallic acid.

Aptamers as described herein may include any number of modifications than can affect the function or affinity of the aptamer. For example, aptamers may be unmodified or they may contain modified nucleotides to improve stability, nuclease resistance or delivery characteristics. Examples of such modifications may include chemical substitutions at the sugar and/or phosphate and/or base positions, for example, at the 2' position of ribose, the 5 position of pyrimidines, and the 8 position of purines, various 2'-modified pyrimidines and modifications with 2'-amino (2'-NH$_2$), 2'-fluoro (2'-F), and/or 2'-O-methyl (2'-OMe) substituents. In some cases, aptamers described herein comprise a 2'-OMe modification to increase in vivo stability. In some cases, the aptamers described herein contain modified nucleotides to improve the affinity and specificity of the aptamers for a vitreous component. Examples of modified nucleotides include those modified with guanidine, indole, amine, phenol, hydroxymethyl, or boronic acid. In other cases, pyrimidine nucleotide triphosphate analogs or CE-phosphoramidites may be modified at the 5 position to generate, for example, 5-benzylaminocarbonyl-2'-deoxyuridine (BndU); 5-[N-(phenyl-3-propyl)carboxamide]-2'-deoxyuridine (PPdU); 5-(N-thiophenylmethylcarboxamide)-2'-deoxyuridine (ThdU); 5-(N-4-fluorobenzylcarboxamide)-2'-deoxyuridine (FBndU); 5-(N-(1-naphthylmethyl)carboxamide)-2'-deoxyuridine (NapdU); 5-(N-2-naphthylmethylcarboxyamide)-2'-deoxyuridine (2NapdU); 5-(N-1-naphthylethylcarboxyamide)-2'-deoxyuridine (NEdU); 5-(N-2-naphthylethylcarboxyamide)-2'-deoxyuridine (2NEdU); 5-(N-tryptaminocarboxyamide)-2'-deoxyuridine (TrpdU); 5-isobutylaminocarbonyl-2'-deoxyuridine (IbdU); 5-(N-tyrosylcarboxyamide)-2'-deoxyuridine (TyrdU); 5-(N-isobutylaminocarbonyl)-2'-deoxyuridine (iBudU); 5-(N-benzylcarboxyamide)-2'-O-methyluridine, 5-(N-benzylcarboxyamide)-2'-fluorouridine, 5-(N-phenethylcarboxyamide)-2'-deoxyuridine (PEdU), 5-(N-3,4-methylenedioxybenzylcarboxyamide)-2'-deoxyuridine (MBndU), 5-(N-imidizolylethylcarboxyamide)-2'-deoxyuridine (ImdU), 5-(N-isobutylcarboxyamide)-2'-O-methyluridine, 5-(N-isobutylcarboxyamide)-2'-fluorouridine, 5-(N—R-threoninylcarboxyamide)-2'-deoxyuridine (ThrdU), 5-(N-tryptaminocarboxyamide)-2'-O-methyluridine, 5-(N-tryptaminocarboxyamide)-2'-fluorouridine, 5-(N-[1-(3-trimethylamonium)propyl]carboxyamide)-2'-deoxyuridine chloride, 5-(N-naphthylmethylcarboxyamide)-2'-O-methyluridine, 5-(N-naphthylmethylcarboxyamide)-2'-fluorouridine, 5-(N-[1-(2,3-dihydroxypropyl)]carboxyamide)-2'-deoxyuridine), 5-(N-2-naphthylmethylcarboxyamide)-2'-O-methyluridine, 5-(N-2-naphthylmethylcarboxyamide)-2'-fluorouridine, 5-(N-1-naphthylethylcarboxyamide)-2'-O-methyluridine, 5-(N-1-naphthylethylcarboxyamide)-2'-fluorouridine, 5-(N-2-naphthylethylcarboxyamide)-2'-O-methyluridine, 5-(N-2-naphthylethylcarboxyamide)-2'-fluorouridine, 5-(N-3-benzofuranylethylcarboxyamide)-2'-deoxyuridine (BFdU), 5-(N-3-benzofuranylethylcarboxyamide)-2'-O-methyluridine, 5-(N-3-benzofuranylethylcarboxyamide)-2'-fluorouridine, 5-(N-3-benzothiophenylethylcarboxyamide)-2'-deoxyuridine (BTdU), 5-(N-3-benzothiophenylethylcarboxyamide)-2'-O-methyluridine, 5-(N-3-benzothiophenylethylcarboxyamide)-2'-fluorouridine; 5-[N-(1-morpholino-2-ethyl)carboxamide]-2'-deoxyuridine (MOEdu); R-tetrahydrofuranylmethyl-2'-deoxyuridine (RTMdU);

3-methoxybenzyl-2'-deoxyuridine (3MBndU); 4-methoxybenzyl-2'-deoxyuridine (4MBndU); 3,4-dimethoxybenzyl-2'-deoxyuridine (3,4DMBndU); S-tetrahydrofuranylmethyl-2'-deoxyuridine (STMdU); 3,4-methylenedioxyphenyl-2-ethyl-2'-deoxyuridine (MPEdU); 4-pyridinylmethyl-2'-deoxyuridine (PyrdU); or 1-benzimidazol-2-ethyl-2'-deoxyuridine (BidU); 5-(amino-1-propenyl)-2'-deoxyuridine; 5-(indole-3-acetamido-1-propenyl)-2'-deoxyuridine; or 5-(4-pivaloylbenzamido-1-propenyl)-2'-deoxyuridine.

Modifications of the aptamers contemplated in this disclosure include, without limitation, those which provide other chemical groups that incorporate additional charge, polarizability, hydrophobicity, hydrogen bonding, electrostatic interaction, and functionality to the nucleic acid aptamer bases or to the nucleic acid aptamer as a whole. Modifications to generate oligonucleotide populations that are resistant to nucleases can also include one or more substitute internucleotide linkages, altered sugars, altered bases, or combinations thereof. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, and unusual base-pairing combinations such as the isobases isocytidine and isoguanosine. Modifications can also include 3' and 5' modifications such as capping, e.g., addition of a 3'-3'-dT cap to increase exonuclease resistance.

The length of the aptamer can be variable. In some cases, the length of the aptamer is less than 100 nucleotides. In some cases, the length of the aptamer is greater than 10 nucleotides. In some cases, the length of the aptamer is between 10 and 90 nucleotides. The aptamer can be, without limitation, about 10, about 15, about 20, about 25, about 30, about 35, about 40, about 45, about 50, about 55, about 60, about 65, about 70, about 75, about 80, about 85, or about 90 nucleotides in length.

In some cases, to enable conjugation of a vitreous component binding aptamer to a therapeutic aptamer, a linker with a reactive moiety can be attached to the aptamer to provide a specific site for conjugation. Various linkers and attachment chemistries are known in the art. In a non-limiting example, 6-(trifluoroacetamido)hexanol (2-cyanoethyl-N,N-diisopropyl)phosphoramidite can be used to add a hexylamino linker to the 5' end of the synthesized aptamer. This linker, as with the other amino linkers provided herein, once the group protecting the amine has been removed, can be reacted with PEG-NHS esters to produce covalently linked PEG-aptamers. Other non-limiting examples of linker phosphoramidites may include: TFA-amino C4 CED phosphoramidite having the structure:

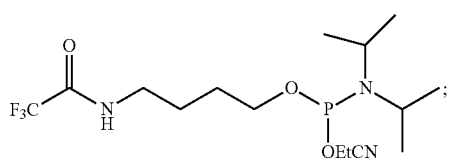

5'-amino modifier C3 TFA having the structure:

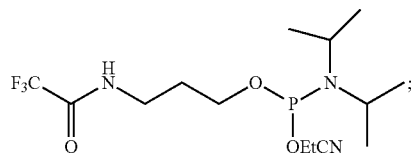

MT amino modifier C6 CED phosphoramidite having the structure:

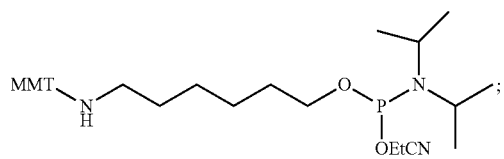

5'-amino modifier 5 having the structure:

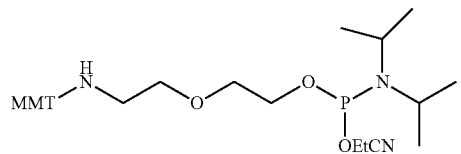

MMT: 4-Monomethoxytrityl

5'-amino modifier C12 having the structure:

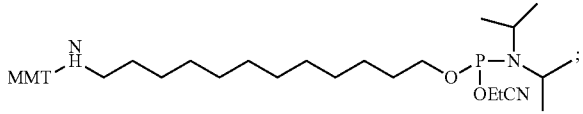

MMT: 4-Monomethoxytrityl and 5' thiol-modifier C6 having the structure:

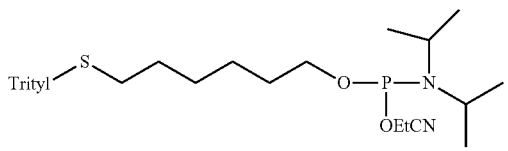

The 5'-thiol modified linker may be used, for example, with PEG-maleimides, PEG-vinylsulfone, PEG-iodoacetamide and PEG-orthopyridyl-disulfide. In one example, the aptamer may be bonded to the 5'-thiol through a maleimide or vinyl sulfone functionality.

Bispecific aptamer compositions consisting of a vitreous component binding (VB) aptamer covalently bonded to a therapeutic (Tx) aptamer can be produced by solid phase oligonucleotide synthesis using standard phosphoramidite chemistry. In one example, the VB aptamer is synthesized on the solid support in a 3' to 5' direction, followed by a joining linker (L) and the Tx aptamer, also in the 3' to 5' direction. This strategy produces a bispecific aptamer of the geometry 5'-Tx-L-VB-3'. Alternatively, the Tx aptamer is first synthesized on the solid support in the 3' to 5' direction, followed by a joining linker and the VB aptamer, also in the 3' to 5' direction. This strategy produces a bispecific aptamer of the geometry 5'-VB-L-Tx-3'. Linkers of the disclosure are generally inert linkers composed of carbon atoms or hexaethylene glycol repeats of <5,000 Da.

In one non-limiting example, the linker used to join the Tx and VB aptamers is 3-(4,4'-Dimethoxytrityloxy)propyl-1-[(2-cyanoethyl)-(N,N-diisopropyl)]-phosphoramidite of the formula:

$$\text{DMTO}\diagup\diagdown\diagup\text{O}-\underset{\underset{\text{O}-\text{CNEt}}{|}}{\text{P}}-\text{N(iPr)}_2$$

which yields a 3-carbon linker upon incorporation into the bispecific aptamer.

In another non-limiting example, the linker used to join the Tx and VB aptamers is 6-(4,4'-Dimethoxytrityloxy) hexanediol-1-[(2-cyanoethyl)-(N,N-diisopropyl)]-phosporamidite of $$\text{DMT}-\text{O}\diagup\diagdown\diagup\diagdown\diagup\text{O}-\underset{\underset{\text{OCE}}{|}}{\text{P}}-\text{N(iPr)}_2$$

the formula:
which yields a 6-carbon linker upon incorporation into the bispecific aptamer.

In another non-limiting example, the linker used to join the Tx and VB aptamers is 8-(4,4'-Dimethoxytrityloxy) triethyleneoxide-1-[(2-cyanoethyl)-(N,N-diisopropyl)]-phosporamidite of the formula:

$$\text{DMT}-\text{O}\diagup\diagdown\text{O}\diagup\diagdown\text{O}\diagup\diagdown\text{O}-\underset{\underset{\text{OCE}}{|}}{\text{P}}-\text{N(iPr)}_2$$

which yields a triethylene glycol linker upon incorporation into the bispecific aptamer.

In another non-limiting example, the linker used to join the Tx and VB aptamers is 17-(4,4'-Dimethoxytrityloxy) hexaethyleneoxide-1-[(2-cyanoethyl)-(N,N-diisopropyl)]-phosporamidite of the formula which yields a hexaethylene glycol linker upon incorporation into the bispecific aptamer.

Bispecific aptamer compositions consisting of a vitreous component binding (VB) aptamer covalently bonded to a therapeutic (Tx) aptamer can be produced by site-specific conjugation using a bifunctional linker. In one example, a reactive moiety such as a thiol is incorporated at the 5' end of the VB aptamer and a different reactive moiety such as a primary amine is incorporated at the 5' end of the Tx aptamer. Conjugation of two such aptamers using a bifunctional linker produces a bispecific aptamer of the geometry 3'-Tx-L-VB-3'. In another example, a reactive moiety such as a thiol is incorporated at the 5' end of the VB aptamer and a different reactive moiety such as a primary amine is incorporated at the 3' end of the Tx aptamer. Conjugation of two such aptamers using a bifunctional linker produces a bispecific aptamer of the geometry 5'-Tx-L-VB-3'. In yet another example, a reactive moiety such as a thiol is incorporated at the 3' end of the VB aptamer and a different reactive moiety such as a primary amine is incorporated at the 3' end of the Tx aptamer. Conjugation of two such aptamers using a bifunctional linker produces a bispecific aptamer of the geometry 5'-Tx-L-VB-5'. Such embodiments are provided by way of example only. Numerous variations, changes, and substitutions may be utilized as needed.

In some instances, a vitreous component binding aptamer can be produced with a C6-disulfide linker and a therapeutic aptamer can be produced with a C6-amino linker and conjugated as follows. The Tx aptamer with the C6-amino linker may be conjugated to a linker consisting of the general formula NHS (N-hydroxysuccinimide)-[PEG]$_n$-maleimide, leaving groups and unreacted linker may be removed by dialysis or a similar method, and then the disulfide of the linker on the vitreous binding aptamer may be reduced, and reacted with the Tx-[PEG-]$_n$-MAL to produce the Tx-[PEG]$_n$-VB bispecific aptamer, which may be subsequently purified by chromatography and desalting. In some cases, this reaction is carried out between about pH 6 and about pH 10, or between pH 7 and 9 or about pH 8 to promote reaction of the NHS ester with the primary amine on the aptamer while maintaining the integrity of the maleimide. Alternatively, the C6-amino linker can be incorporated into the VB aptamer and the C6-disulfide linker into the Tx aptamer and the conjugation performed in a similar manner.

In one non-limiting example, the linker used to conjugate the Tx and VB aptamers is maleimide-PEG$_2$-succinimidyl ester of the formula:

which yields a diethylene glycol linker upon formation of the bispecific aptamer.

In another non-limiting example, the linker used to conjugate the Tx and VB aptamers is maleimide-PEG$_4$-succinimidyl ester of the formula:

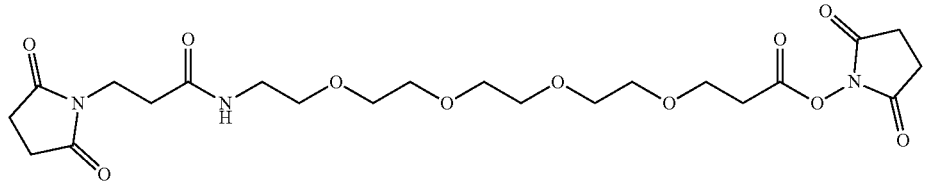 [SMILES: O=C(CCN1C(=O)CCC1=O)NCCOCCOCCOCCOCCC(=O)ON1C(=O)CCC1=O]

which yields a tetraethylene glycol linker upon formation of the bispecific aptamer.

In another non-limiting example, the linker used to conjugate the Tx and VB aptamers is maleimide-PEG$_8$-succinimidyl ester of the formula:

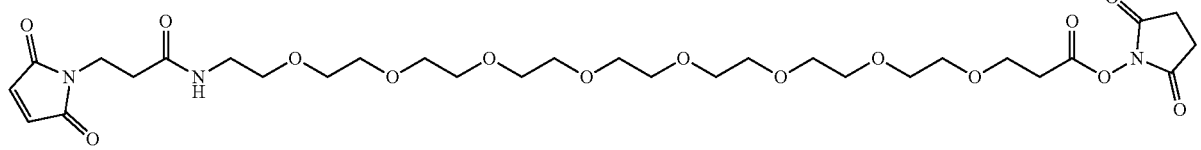

which yields an octaethylene glycol linker upon formation of the bispecific aptamer.

In another non-limiting example, the linker used to conjugate the Tx and VB aptamers is maleimide-PEG$_{12}$-succinimidyl ester of the formula:

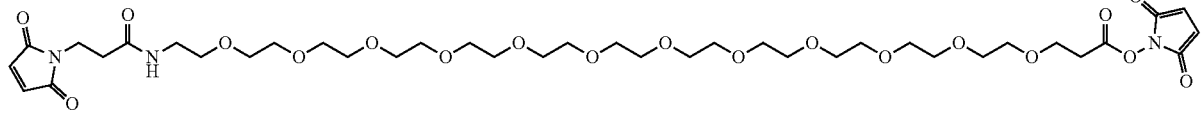

which yields a dodecaethylene glycol linker upon formation of the bispecific aptamer.

In another non-limiting example, the linker used to conjugate the Tx and VB aptamers is maleimide-PEG$_{24}$-succinimidyl ester of the formula:

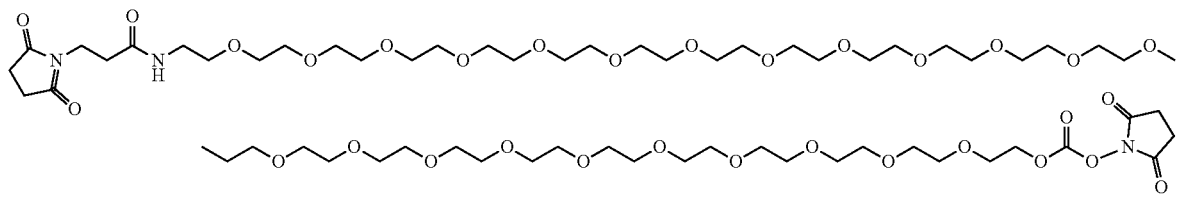

which yields a tetracosaethylene glycol linker upon formation of the bispecific aptamer. Such embodiments are provided by way of example only. Numerous variations, changes, and substitutions may be utilized as needed.

In some aspects, the therapeutic agent and the vitreous component binding moiety are directly conjugated (e.g., in the absence of a linker). In other aspects, the therapeutic agent and the vitreous component binding moiety are conjugated by way of a linker as described herein.

In some cases, the vitreous component binding aptamers described herein may be bound or conjugated to one or more molecules having desired biological properties. Any number of molecules can be bound or conjugated to aptamers, non-limiting examples including antibodies, peptides, proteins, carbohydrates, enzymes, polymers, drugs, small molecules, gold nanoparticles, radiolabels, fluorescent labels, dyes, haptens (e.g., biotin), other aptamers, or nucleic acids (e.g., siRNA). In some cases, aptamers may be conjugated to molecules that increase the stability, the solubility or the bioavailability of the aptamer. Non-limiting examples include polyethylene glycol (PEG) polymers, carbohydrates and fatty acids. In some cases, molecules that improve the transport or delivery of the aptamer may be used, such as cell penetration peptides. Non-limiting examples of cell penetration peptides can include peptides derived from Tat, penetratin, polyarginine peptide Arg$_8$ sequence, Transportan, VP22 protein from Herpes Simplex Virus (HSV), antimicrobial peptides such as Buforin I and SynB, polyproline sweet arrow peptide molecules, Pep-1 and MPG. In some embodiments, the aptamer is conjugated to a lipophilic compound such as cholesterol, dialkyl glycerol, diacyl glycerol, or non-immunogenic water-soluble pharmaceutically acceptable polymers.

In some cases, the aptamer formulated according to the present disclosure may also be modified by encapsulation within a liposome. In other cases, the aptamer formulated according to the present disclosure may also be modified by encapsulation within a micelle. Liposomes and micelles may be comprised of any lipids, and in some cases the lipids may be phospholipids, including phosphatidylcholine.

In some examples, the compositions are designed to lose their vitreous binding ability, for example, by degradation of the vitreous component binding moiety. In other examples, the compositions are designed such that the therapeutic agent can dissociate from the vitreous component binding moiety. This may be accomplished by introducing one or more cleavable bonds between the therapeutic agent and the vitreous component binding moiety. The one or more cleavable bonds may be cleaved by, e.g., an enzyme, a chemical or may naturally degrade to release the therapeutic agent from the vitreous.

The compositions herein generally include one or more therapeutic agents. The one or more therapeutic agents may be conjugated to the one or more vitreous component binding moieties. Conjugated can mean covalently bound or non-covalently bound. The therapeutic agent may be any therapeutic agent used for the treatment of a disease. In some cases, the therapeutic agent is used for the treatment of a retinal disease.

Often, the compositions described herein generally have a molecular weight less than 50 kDa. For example, the compositions may have a molecular weight of less than 10 kDa, less than 20 kDa, less than 25 kDa, less than 30 kDa, less than 35 kDa, less than 40 kDa, or less than 45 kDa.

In some cases, the compositions described herein may have a molecular weight greater than at least 1 kDa and often substantially greater than 1 kDa. For example, the compositions may have a molecular weight of at least 10 kDa, at least 20 kDa, at least 30 kDa, at least 40 kDa, at least 50 kDa, at least 60 kDa, at least 70 kDa, at least 80 kDa, at least 90 kDa, at least 100 kDa, at least 120 kDa, at least 140 kDa, at least 160 kDa, at least 180 kDa, at least 200 kDa or greater than 200 kDa.

The mean residence time may refer to the average amount of time a composition of the disclosure remains in the vitreous after injection. The mean residence time of the composition may be dependent on a number of factors including IVT half-life. In some aspects, the composition has an increased or improved IVT mean residence time relative to an unconjugated therapeutic agent. A therapeutic agent conjugated to one or more vitreous component binding moieties as described herein may exhibit 10%, 20%, 30%, 40%, 50%, 60%, 70%, 80%, 85%, 90%, 95%, 96%, 97%, 98%, 99% or greater than 99% longer mean residence time relative to its unconjugated equivalent. In some cases, the mean residence time of the compositions herein is on the order of at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 25 days, at least 30 days or greater than 30 days.

In some cases, the aptamers described herein have an intraocular half-life of at least 1 day in a non-human animal (e.g., rodent/rabbit/non-human primate). In some cases, the aptamers described herein have an intraocular half-life of at least 1 day, at least 2 days, at least 3 days, at least 4 days, at least 5 days, at least 6 days, at least 7 days, at least 8 days, at least 9 days, at least 10 days or greater in a non-human animal such as a rodent, rabbit or non-human primate. In a particular example, the aptamers described herein have an intraocular half-life of at least 2 days in a rabbit. In another particular example, the aptamers described herein have an intraocular half-life of at least 3 days in a non-human primate.

In some aspects, the compositions provided herein may have properties superior to formulations that use high molecular weight molecules (e.g., 40 kDa or greater than 40 kDA polyethylene glycol (PEG) polymers) to promote intravitreal retention. In some cases, a composition provided herein has similar or better intraocular retention time as compared to a composition comprising a PEG molecule, yet has less viscosity (e.g., less than 10%, 20%, 30%, 40%, 50%, or greater than 50%) than the composition comprising the PEG molecule when similarly formulated. In some cases, a composition provided herein has an intraocular half-life of at least 2 days, of at least 3 days, of at least 4 days, of at least 5 days, of at least 6 days, or of at least 7 days in a mammalian system, yet is provided in a formulation having less than 50% of the viscosity of a similar formulation containing a 40 kDa PEG.

In some aspects, the composition has an increased or improved IVT half-life relative to an unconjugated therapeutic agent. For example, a therapeutic agent conjugated to one or more vitreous component binding moieties as described herein may exhibit 10%, 20%, 30%, 40%, 50%, 60%, 70%, 80%, 85%, 90%, 95%, 96%, 97%, 98%, 99% or greater than 99% longer IVT half-life relative to its unconjugated equivalent. In some cases, the IVT half-life of the compositions herein is on the order of at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 25 days, at least 30 days or greater than 30 days.

In some cases, the compositions described herein include a therapeutic agent conjugated to one or more vitreous component binding moieties. The therapeutic agent can be, without limitation, a small molecule, an antibody or derivative thereof, a peptide, an aptamer, and the like. In some cases, the therapeutic agent is an aptamer. In other cases, the therapeutic agent is an antibody.

In some cases, the therapeutic agent may have antagonistic activity (e.g., inhibit the function of a protein). In other cases, the therapeutic agent may have agonistic activity (e.g., enhance or increase the function of a protein). The therapeutic agent may modulate or alter the function of a biological cell (e.g., a retinal cell). The therapeutic agent may modulate or alter the function of a protein or other component of the vitreous.

In some cases, the therapeutic agent is an inhibitor of vascular endothelial growth factor (VEGF) or VEGF signaling. The therapeutic agent can be any type of molecule that decreases the ability of VEGF to exert its normal biological effect. For example, the compound may bind and inhibit, or reduce the production of VEGF per se, a receptor thereof, or an intracellular signaling protein or transcription factor activated and/or synthesized upon VEGF receptor activation following binding by VEGF. In some cases, the therapeutic agent is an anti-VEGF or anti-VEGFR aptamer or antibody. Non-limiting examples of therapeutic agents that may be used in the compositions described herein include, quinazoline derivative inhibitors of VEGFs (as described in U.S. Patent Publication Nos. 2007/265286, 2003/199491 and U.S. Pat. No. 6,809,097), quercetin (as described in WO 02/057473), quinazoline derivative inhibitors of VEGFR tyrosine kinases (as described in U.S. Patent Publication No. 2007/027145), aminobenzoic acid derivative inhibitors of VEGFR tyrosine kinases (as described in U.S. Pat. No. 6,720,424), pyridine derivative inhibitors of VEGFR tyrosine kinases (as described in U.S. Patent Publication No. 2003/158409), cediranib (as described in WO 07/060402), sunitinib (described in WO 08/031835 and U.S. Pat. No. 6,573,293), pegaptanib (described in U.S. Pat. No. 6,051,698), axitinib (as described in WO 2004/087152, sorafenib (described in WO 07/053573), VEGFR-I binding peptides (described in U.S. Patent Publication No. 2005/100963), arginine-rich anti-vascular endothelial growth factor peptides that block VEGF binding to receptors (described in U.S. Pat. No. 7,291,601), VEGF-Trap (as marketed by Regeneron Pharmaceuticals and described in U.S. Patent Publication No. 2005/032699), soluble VEGF receptors (as described in U.S. Patent Publication No. 2006/110364 and Tseng et al., 2002), VEGF-C and VEGF-D peptidomimetic inhibitors (as described in U.S. Patent Publication No. 2002/065218), PAI-I (as described in U.S. Patent Publication No. 2004/121955), and inhibitors described in U.S. Patent Publication No. 2002/068697, WO 02/081520, U.S. Patent Publication No. 20060234941, and U.S. Patent Publication No. 2002/058619. In some cases, the therapeutic agent is an antibody or antibody-related molecule or fragment thereof, including, without limitation, anti-VEGF-A antibodies such as bevacizumab (as described in U.S. Pat. No. 6,054,297), ranibizumab (as described in U.S. Pat. No. 6,407,213) as well as those described in U.S. Pat. No. 5,730,977 and U.S. Patent Publication No. 2002/032315; anti-VEGF-B antibodies including those described in U.S. Patent Publication No. 2004/005671 and WO 07/140534; anti-VEGF-C antibodies including those described in U.S. Pat. No. 6,403,088; anti-VEGF-D antibodies including those described in U.S. Pat. No. 7,097,986; anti-VEGFR-1 antibodies including those described in U.S. Patent Publication No. 2003/088075; anti-VEGFR-2 antibodies including those described in U.S. Pat. No. 6,344,339; WO 99/40118 and U.S. Patent Publication No. 2003/176674; and anti-VEGFR-3 antibodies including those described in U.S. Pat. No. 6,824,777.

In some aspects, a composition of the disclosure is a bi-specific aptamer comprising an anti-VEGF aptamer coupled to an anti-hyaluronan aptamer. In some cases, the HA-VEGF bi-specific aptamer comprises a sequence as described in Table 2 below.

(PDGFR), or a signaling pathway associated with either. In some cases, the therapeutic agent is an anti-PDGF aptamer or antibody. Non-limiting examples of these types of therapeutic agents include imatinib, imatinib mesylate, tyrphostin A23, tyrphostin AG 1295, tyrphostin 9, AG494, masitinib, AP24534, motesanib diphosphate, DMPQ dihydrochloride, oxindole I, AG-370, RG-13022, 3-(4-Isopropylbenzylidenyl)-indolin-2-one, tivozanib, PP121, (5-hydroxy-1H-indol-2-yl)-(1H-indol-2-yl)methanone; (5-Butanoate-1H-2-indolyl)(1H-2-indolyl)-methanone; sunitinib malate, 4-(6,7-dimethoxyquinazolin-4-yl)-N-(4-phenoxyphenyl) piperazine-1-carboxamide; semaxanib; pazopanib hydrochloride; pazopanib; PD 161570; dovitinib; tyrphostin 47; and 4,4'-Bis(4-aminophenoxy)biphenyl.

In some aspects, a composition of the disclosure is a bi-specific aptamer comprising an anti-PDGF aptamer coupled to an anti-hyaluronan aptamer. In some cases, the

TABLE 2

Aptamer Sequences

| SEQ ID NO: | Aptamer Number | Backbone | Sequence (5' to 3') |
|---|---|---|---|
| SEQ ID NO: 12 | Aptamer 12 | RNA | C6NH$_2$fCmGmGrArAfUfCmAmGfUmG mAmAfUmGfCfUfUmAfUmAfCmAfUf CfCmGidT; where mG or mA is 2'Omethyl RNA; fC or fU is 2'fluoro RNA; rG or rA is 2'OH RNA; idT is inverted deoxythymidine |
| SEQ ID NOs: 13 and 16 | Aptamer 13 | DNA/ RNA | CACTTCATGTAAGACTAAAAGATG GAGCGTGAAGGATGCA[ISp18]fCmG mGrArAfUfCmAmGfUmGmAmAfUmG fCfUfUmAfUmAfCmAfUfCfCmGidT; where [ISp18] is an 18 atom hexaethylene glycol spacer; mG or mA is 2'Omethyl RNA; fC or fU is 2'fluoro RNA; rG or rA is 2'OH RNA; idT is inverted deoxythymidine |

In some cases, the therapeutic agent is an inhibitor of platelet-derived growth factor (PDGF), a PDGF receptor HA-PDGF bi-specific aptamer comprises a sequence as described in Table 3 below.

TABLE 3

Aptamer Sequences

| SEQ ID NO. | Aptamer Number | Backbone | Sequence (5' to 3') |
|---|---|---|---|
| SEQ ID NOs: 8, 17, and 18 | Aptamer 8 | DNA/ RNA | C6NH$_2$CAGGCfUAfCmG[ISp18]CG TAmGAmGCAfUfCmA[ISp18]TGA TfCfCfUmGidT; where [ISp18] is an 18 atom hexaethylene glycol spacer; mG or mA is 2'Omethyl RNA; fC or fU is 2'fluoro RNA; idT is inverted deoxythymidine |
| SEQ ID NOs: 9 and 19-21 | Aptamer 9 | DNA/ RNA | TGGCAAGTATTTGTACATATACT GACGTTTGCCGTACTGC[ISp18]C AGGCfUAfCmG[ISp18]CGTAmGA mGCAfUfCmA[ISp18]TGATfCfCfU mGidT; where [ISp18] is an 18 atom hexaethylene glycol spacer; mG or mA is 2'Omethyl RNA; fC or fU is |

TABLE 3-continued

Aptamer Sequences

| SEQ ID NO. | Aptamer Number | Backbone | Sequence (5' to 3') |
|---|---|---|---|
| | | | 2'fluoro RNA; idT is inverted deoxythymidine |
| SEQ ID NOs: 10, 22, and 23 | Aptamer 10 | DNA/ RNA | CACTTCATGTAAGACTAAAAGA TGGAGCGTGAAGGATGCACAGG CfUAfCmG[ISp18]CGTAmGAmGC AfUfCmA[ISp18]TGATfCfCfUmGid T; where [ISp18] is an 18 atom hexaethylene glycol spacer; mG or mA is 2'Omethyl RNA; fC or fU is 2'fluoro RNA; idT is inverted deoxythymidine |
| SEQ ID NOs: 11, 24, and 25 | Aptamer 11 | DNA/ RNA | TCCTTTAGAGTGGCGAAGTACC TAATACAACCTAAAATCCCAGG CfUAfCmG[ISp18]CGTAmGAmGC AfUfCmA[ISp18]TGATfCfCfUmGid T; where [ISp18] is an 18 atom hexaethylene glycol spacer; mG or mA is 2'Omethyl RNA; fC or fU is 2'fluoro RNA; idT is inverted deoxythymidine |

In some cases, the therapeutic agent is an inhibitor of hypoxia-inducible factor 1 (HIF-1). In some cases, the therapeutic agent is an inhibitor of HIF-1α, the inducible subunit of HIF-1. In some cases, the therapeutic agent is an anti-HIF-1 aptamer or antibody. Non-limiting examples of therapeutic agents that target HIF-1 may include echinomycin; BDDF-I (as described in WO 08/004798); S-2-amino-3-[4'-N,N,-bis(2-chloroethyl)amino]phenyl propionic acid N-oxide dihydrochloride (PX-478) (as described in U.S. Patent Publication No. 2005049309); chetomin; 3-(5'-hydroxymethyl-2'-furyl)-1-benzylindazole (YC-I); 103D5R; quinocarmycin monocitrate and derivatives thereof; 3-(5'-hydroxymethyl-2'-furyl)-1-benzylindazole (as described in U.S. Patent Publication No. 2004198798); NSC-134754; NSC-643735; digoxin; rapamycin; 2-methoxyestradiol; topotecan; LAQ824; 17-AAG; cyclosporine; acriflavine; doxorubicin; bortezomib; amphotericin B; imatinib; ibuprofen; erlotinib; gefitinib and trastuzumab.

In other examples, the therapeutic agent is an inhibitor of an alternative complement pathway component. For example, the therapeutic agent may be an inhibitor of complement Factor D, Factor P, complement component 3 (C3), or complement component 5 (C5). In some examples, the therapeutic agent is an anti-Factor D or anti-Factor P aptamer. In other examples, the therapeutic agent is an anti-Factor D or anti-Factor P antibody or antibody derivative or fragment thereof. Inhibitors of the alternative complement pathway may be suitable for treatment of, e.g., age-related macular degeneration, including dry age-related macular degeneration and advanced types including geographic atrophy. In some cases, the therapeutic agent is an agonist of a complement pathway component such as Factor H or Factor I.

In some aspects, a composition of the disclosure is a bi-specific aptamer comprising an anti-C5 aptamer coupled to an anti-hyaluronan aptamer. In some cases, an HA-05 bi-specific aptamer comprises a sequence as described in Table 4 below.

TABLE 4

Aptamer Sequences

| SEQ ID NO. | Aptamer Number | Backbone | Sequence (5' to 3') |
|---|---|---|---|
| SEQ ID NO: 14 | Aptamer 14 | RNA | C6NH₂fCmGfCfCrGfCmGmGfUfC fUfCmAmGmGfCrGfCfUmGmAm GfUfCfUmGmAmGfUfUfUrAfCfC fUmGfCmGidT; where mG or mA is 2'Omethyl RNA; fC or fU is 2'fluoro RNA; rG or rA is 2'OH RNA; idT is inverted deoxythymidine |
| SEQ ID NOs: 15 and 26 | Aptamer 15 | DNA/ RNA | TCCTTTAGAGTGGCGAAGTAC CTAATACAACCTAAAATCC[ISp18] fCmGfCfCrGfCmGmGfUfCfUf CmAmGmGfCrGfCfUmGmAmGf UfCfUmGmAmGfUfUfUrAfCfCfU mGfCmGidT; |

TABLE 4-continued

Aptamer Sequences

| SEQ ID NO. | Aptamer Number | Backbone | Sequence (5' to 3') |
|---|---|---|---|
| | | | where [ISp18] is an 18 atom hexaethylene glycol spacer; mG or mA is 2'Omethyl RNA; fC or fU is 2'fluoro RNA; rG or rA is 2'OH RNA; idT is inverted deoxythymidine |

In some cases, an aptamer of the disclosure comprises an oligonucleotide having a sequence according to any one of SEQ ID NOs 8, 17, and 18; 9 and 19-21; 10, 22, and 23; 11, 24, and 25; 12; 13 and 16; 14; or 15 and 26; or an oligonucleotide sequence having at least 80% sequence identity of any one of SEQ ID NOs 8, 17, and 18; 9 and 19-21; 10, 22, and 23; 11, 24, and 25; 12; 13 and 16; 14; or 15 and 26. It should be understood that where a DNA backbone has been recited, said DNA may be substituted with one or more types of nucleic acids selected from the group consisting of: modified RNA and modified DNA; and where an RNA backbone has been recited, said RNA may be substituted with one or more types of nucleic acids selected from the group consisting of: modified RNA, DNA, and modified DNA.

In some cases, an aptamer of the disclosure may have at least 80%, 81%, 82%, 83%, 84%, 85%, 86%, 87%, 88%, 89%, 90%, 91%, 92%, 93%, 94%, 95%, 96%, 97%, 98%, or 99% sequence identity with any aptamer described herein. For example, an aptamer of the disclosure may have at least 80%, 81%, 82%, 83%, 84%, 85%, 86%, 87%, 88%, 89%, 90%, 91%, 92%, 93%, 94%, 95%, 96%, 97%, 98%, or 99% sequence identity with any aptamer described in Tables 2-4. In some cases, an aptamer of the disclosure may have at least 80%, 81%, 82%, 83%, 84%, 85%, 86%, 87%, 88%, 89%, 90%, 91%, 92%, 93%, 94%, 95%, 96%, 97%, 98%, or 99% sequence homology with any aptamer described herein. For example, an aptamer of the disclosure may have at least 80%, 81%, 82%, 83%, 84%, 85%, 86%, 87%, 88%, 89%, 90%, 91%, 92%, 93%, 94%, 95%, 96%, 97%, 98%, or 99% sequence homology with any aptamer described in Tables 2-4.

Therapeutic agents can be directed to essentially any biological target to treat retinal disease. Other non-limiting examples of biological targets may include Angiopoietin-2 (Ang2), interleukins including IL-2, IL-6 and IL-8, and integrins.

Other non-limiting examples of therapeutic agents, any of which are suitable for use in the compositions described herein include: thrombin inhibitors; antithrombogenic agents; thrombolytic agents (such as plasminogen activator, or TPA and streptokinase); fibrinolytic agents; vasospasm inhibitors; calcium channel blockers; vasodilators; antihypertensive agents; clotting cascade factors (for example, protein S); anti-coagulant compounds (for example, heparin and nadroparin, or low molecular weight heparin); antimicrobial agents, such as antibiotics (such as tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate, minocycline, doxycycline, vancomycin, kanamycin, cephalosporins such as cephalothin, cephapirin, cefazolin, cephalexin, cephardine, cefadroxil, cefamandole, cefoxitin, cefaclor, cefuroxime, cefonicid, ceforanide, cefitaxime, moxalactam, cetizoxime, ceftriaxone, cefoperazone), geldanamycin and analogues, antifungals (such as amphotericin B and miconazole), and antivirals (such as idoxuridine trifluorothymidine, acyclovir, gancyclovir, interferon, α-methyl-P-adamantane methylamine, hydroxy-ethoxymethyl-guanine, adamantanamine, 5-iodo-deoxyuridine, trifluorothymidine, interferon, adenine arabinoside); inhibitors of surface glycoprotein receptors; antiplatelet agents (for example, ticlopidine); antimitotics; microtubule inhibitors; anti-secretory agents; active inhibitors; remodeling inhibitors; antisense nucleotides (such as morpholino phosphorodiamidate oligomer); anti-metabolites; antiproliferatives (including antiangiogenesis agents, taxol, sirolimus (rapamycin), analogues of rapamycin ("rapalogs"), tacrolimus, ABT-578 from Abbott, everolimus, paclitaxel, taxane, vinorelbine); anticancer chemotherapeutic agents; anti-inflammatories (such as hydrocortisone, hydrocortisone acetate, dexamethasone 21-phosphate, fluocinolone, medrysone, methylprednisolone, prednisolone 21-phosphate, prednisolone acetate, fluorometalone, betamethasone, triamcinolone, triamcinolone acetonide); non-steroidal anti-inflammatories (such as salicylate, indomethacin, ibuprofen, diclofenac, flurbiprofen, piroxicam); antiallergenics (such as sodium chromoglycate, antazoline, methapyriline, chlorpheniramine, cetrizine, pyrilamine, prophenpyridamine); anti-proliferative agents (such as 1,3-cis retinoic acid); decongestants (such as phenylephrine, naphazoline, tetrahydrazoline); miotics and anti-cholinesterase (such as pilocarpine, salicylate, carbachol, acetylcholine chloride, physostigmine, eserine, diisopropyl fluorophosphate, phospholine iodine, demecarium bromide); mydriatics (such as atropine, cyclopentolate, homatropine, scopolamine, tropicamide, eucatropine, hydroxyamphetamine); sympathomimetics (such as epinephrine); antineoplastics (such as carmustine, cisplatin, fluorouracil); immunological drugs (such as vaccines and immune stimulants); hormonal agents (such as estrogens, estradiol, progesterol, progesterone, insulin, calcitonin, parathyroid hormone, peptide and vasopressin hypothalamus releasing factor); beta adrenergic blockers (such as timolol maleate, levobunolol HCl, betaxolol HCl); immunosuppressive agents, growth hormone antagonists, growth factors (such as epidermal growth factor, fibroblast growth factor, platelet derived growth factor, transforming growth factor beta, somatotropin, fibronectin, insulin-like growth factor (IGF)); carbonic anhydrase inhibitors (such as dichlorophenamide, acetazolamide, methazolamide); inhibitors of angiogenesis (such as angiostatin, anecortave acetate, thrombospondin, anti-VEGF antibody such as anti-VEGF fragment—ranibizumab); dopamine agonists; radiotherapeutic agents; peptides; proteins; enzymes; nucleic acids and nucleic acid fragments; extracellular matrix components; ACE inhibitors; free radical scavengers; chelators; antioxidants; anti-polymerases; photodynamic therapy agents; gene therapy agents; and other therapeutic agents such as prostaglandins, antiprostaglandins, prostaglandin precursors, and the like.

In some cases, the therapeutic agent is an antiseptic. Non-limiting examples of antiseptics include silver sulfadiazine, chlorhexidine, glutaraldehyde, peracetic acid, sodium hypochlorite, phenols, phenolic compounds, iodophor compounds, quaternary ammonium compounds, and chlorine compounds.

In some cases, the therapeutic agent is an enzyme inhibitor. Non-limiting examples of enzyme inhibitors include chrophonium chloride; N-methylphysostigmine; neostigmine bromide; physostigmine sulfate; tacrine HCL; tacrine; 1-hydroxymaleate; iodotubercidin; p-bromotetramisole; 10-(α-diethylaminopropionyl)-phenothiazine hydrochloride; calmidazoliurn chloride; hemicholinium-3,3,5-dinitrocatechol; diacylglycerol kinase inhibitor 1; diacylglycerol kinase inhibitor II; 3-phenylpropargylamine; N-monomethyl-L-arginine acetate; carbidopa; 3-hydroxybenzylhydrazine HCl; hydralazine HCl; clorgyline HCl; deprenyl HCl; L(−)deprenyl HCl; iproniazid phosphate; 6-MeO-tetrahydro-9H-pyrido-indole; nialamide; pargyline HCl; quinacrine HCl; semicarbazide HCl; tranylcypromine HCl; N,N-diethylaminoethyl-2,2-diphenylvalerate hydrochloride; 3-isobutyl-1-methylxanthine; papaverine HCl, indomethacin; 2-cyclooctyl-2-hydroxyethylamine hydrochloride; 2,3-dichloro-α-methylbenzylamine (DCMB); 8,9-dichloro-2,3,4,5-tetrahydro-1H-2-benzazepine hydrochloride; p-aminoglutethimide; p-aminoglutethimide tartrate; R(+) p-aminoglutethimide tartrate; S(−)3-iodotyrosine; alpha-methyltyrosine; L(−)alpha methyltyrosine; D,L(−)cetazolamide; dichlorophenamide; 6-hydroxy-2-benzothiazolesulfonamide; and allopurinol.

In some cases, the therapeutic agent is an anti-pyretic or anti-inflammatory agent. Non-limiting examples of anti-pyretic or anti-inflammatory agents include aspirin (salicylic acid), indomethacin, sodium indomethacin trihydrate, salicylamide, naproxen, colchicine, fenoprofen, sulindac, diflunisal, diclofenac, indoprofen and sodium salicylamide.

In some cases, the therapeutic agent is a local anesthetic, for example, a substance that has an anesthetic effect in a localized region. Non-limiting examples of local anesthetics include procaine, lidocaine, tetracaine and dibucaine.

Pharmaceutical Compositions

The compositions herein may include any number of pharmaceutical compositions for the treatment of retinal diseases. The pharmaceutical compositions may include a therapeutically effective amount of any composition as described herein (e.g., a therapeutic agent conjugated to one or more vitreous component binding moieties). The term "therapeutically effective amount" refers to an amount of the composition that provokes a therapeutic or desired response in a subject. The pharmaceutical composition may further include any number of excipients, vehicles or carriers. For example, the pharmaceutical composition may include an effective amount of the composition, alone or in combination, with one or more vehicles (e.g., pharmaceutically acceptable compositions or e.g., pharmaceutically acceptable carriers). Excipients may include any and all solvents, lubricants, preservatives, diluents, and vehicles (or carriers). Generally, the excipient is compatible with the compositions described herein. The pharmaceutical composition may also contain minor amounts of non-toxic auxiliary substances such as wetting or emulsifying agents, pH buffering agents, and other substances such as, for example, sodium acetate, and triethanolamine oleate.

The pharmaceutical compositions herein generally may be administered by injection to the vitreous (i.e., intravitreal (IVT) administration). IVT administration may be to one eye if only one eye is affected by the retinal disease, or to both eyes if both eyes are affected. The pharmaceutical compositions herein may be in a formulation suitable for intravitreal administration. For example, the pharmaceutical compositions may be prepared in a liquid formulation for injection into the vitreous.

Liquid formulations provided herein may have low viscosity, e.g., a viscosity amenable to intravitreal injection, yet may also contain a relatively high concentration of aptamer or bi-specific aptamer (e.g., greater than 5 mg/ml, greater than 10 mg/ml, greater than 20 mg/ml, greater than 30 mg/ml, greater than 40 mg/ml, greater than 80 mg/ml, greater than 100 mg/ml, greater than 150 mg/ml, or higher). In a specific example, a liquid formulation provided herein may have a concentration of aptamer or bi-specific aptamer of greater than 30 mg/ml when formulated for intravitreal administration. The dynamic viscosity of a dosage form (or concentration) provided herein may be about 38,800 centipoise to about 194,100 centipoise, about 97,000 centipoise to about 485,500 centipoise, or about 194,100 centipoise to about 970,800 centipoise when formulated in a 50 µL volume and administered with a ½ inch 27-gauge needle. For example, the dynamic viscosity of a dosage form (or concentration) provided herein may be about 25,000; 50,000; 75,000; 100,000; 150,000; 200,000; 250,000; 300,000; 350,000; 400,000; 450,000; 500,000; 550,000; 600,000; 650,000; 700,000; 750,000; 800,000; 850,000; 900,000; 950,000; or 1,000,000 when formulated in a 50 µL volume and administered with a ½ inch 27-gauge needle. The dynamic viscosity of a dosage form (or concentration) provided herein may be about 13,100 centipoise to about 65,000 centipoise, about 32,700 centipoise to about 164,000 centipoise, or about 65,000 centipoise to about 325,000 centipoise when formulated in a 50 µL volume and administered with a ½ inch 30-gauge needle. For example, the dynamic viscosity of a dosage form (or concentration) provided herein may be about 10,000; 20,000; 30,000; 40,000; 50,000; 60,000; 70,000; 80,000; 90,000; 100,000; 150,000; 200,000; 250,000; 300,000; or 350,000 centipoise when formulated in a 50 µL volume and administered with a ½ inch 30-gauge needle. Similarly, the dynamic viscosity of a dosage form (or concentration) provided herein may be about 2,800 centipoise to about 14,500 centipoise, about 7,300 centipoise to about 36,500 centipoise, or about 14,500 to about 75,000 centipoise when formulated in a 50 µL volume and administered with a ½ inch 33-gauge needle. For example, the dynamic viscosity of a dosage form (or concentration) provided herein may be about 2,000; 3,000; 4,000; 5,000; 6,000; 7,000; 8,000; 9,000; 10,000; 15,000; 20,000; 25,000; 30,000; 35,000; 40,000; 45,000; 50,000; 55,000; 60,000; 65,000; 70,000; or 75,000 centipoise when formulated in a 50 µL volume and administered with a ½ inch 33-gauge needle. In some cases, a liquid formulation as provided herein is formulated in a pre-filled syringe. In some cases, a liquid formulation is formulated in a volume of 10 µL, 20 µL, 30 µL, 40 µL, 50 µL, 60 µL, 70 µL, 80 µL, 90 µL, 100 µL or greater than 100 µL.

Other formulations suitable for delivery of the pharmaceutical compositions described herein may include a sustained release gel or polymer formulations by surgical implantation of a biodegradable microsize polymer system, e.g., microdevice, microparticle, or sponge, or other slow release transscleral devices, implanted during the treatment of an ophthalmic disease, or by an ocular delivery device, e.g. polymer contact lens sustained delivery device. In some cases, the formulation is a polymer gel, a self assembling gel, a durable implant, an eluting implant, a biodegradable matrix or a biodegradable polymer. In some cases, the formulation may be administered by iontophoresis using electric current to drive the composition from the surface to the posterior of the eye. In some cases, the formulation may be administered by a surgically implanted port with an intravitreal reservoir, an extra-vitreal reservoir or a combination thereof. Examples of implantable ocular devices can include, without limitation, the Durasert™ technology developed by Bausch & Lomb, the ODTx device developed by On Demand Therapeutics, the Port Delivery System developed by ForSight VISION4 and the Replenish Micro-Pump™ System developed by Replenish, Inc. In some cases, nanotechnologies can be used to deliver the pharmaceutical compositions including nanospheres, nanoparticles, nanocapsules, liposomes, nanomicelles and dendrimers.

A formulation provided herein may contain a concentration of a composition provided herein (e.g., bispecific aptamer) of at least 0.1 mg/ml, 0.5 mg/ml, 1 mg/ml, 2 mg/ml, 3 mg/ml, 5 mg/ml, 10 mg/ml, 25 mg/ml, 50 mg/ml, 60 mg/ml, 70 mg/ml, 80 mg/ml, 90 mg/ml, 100 mg/ml, 110 mg/ml, 120 mg/ml, 130 mg/ml, 140 mg/ml, 150 mg/ml, 200 mg/ml or greater. A formulation provided herein may contain a concentration of a composition provided herein (e.g., a bispecific aptamer) of at least 5 µM, 10 µM, 20 µM, 30 µM, 40 µM, 50 µM, 60 µM, 70 µM, 80 µM, 90 µM, 100 µM, 200 µM, 300 µM, 400 µM, 500 µM, 600 µM, 700 µM, 800 µM, 900 µM, 1 mM, 2 mM, 3 mM, 4 mM, 5 mM, 6 mM, 7 mM, 8 mM, 9 mM, 10 mM or greater than 10 mM. In some cases, a formulation is administered to a subject such that the subject receives a therapeutically effective dose in a single administration, even when a relatively low total volume is administered to the eye. In some cases, a therapeutically effective dose (e.g., greater than 2 mg, greater than 3 mg, greater than 5 mg, greater than 10 mg, greater than 20 mg, or more) is administered to a subject in a total volume of 15 µl to about 100 µl, e.g., 15 µl, 25 µl, 30 µl, 40 µl, 50 µl, 60 µl, 70 µl, 80 µl, 90 µl, 100 µl. In some cases the total volume is less than 150 µl, less than 125 µl, less than 100 µl, less than 90 µl, less than 80 µl, less than 70 µl, less than 60 µl, less than 50 µl, less than 40 µl, less than 30 µl, or less than 20 µl.

The therapeutic agents described herein, by conjugation to one or more vitreous component binding moieties, may exhibit improved intravitreal half-life when compared to their unconjugated counterparts. Thus, pharmaceutical compositions including these therapeutic agents may need to be administered less frequently than unconjugated therapeutic agents. The pharmaceutical compositions herein can be administered once every week, once every 2 weeks, once every 3 weeks, once every 4 weeks, once every 5 weeks, once every 6 weeks, once every 7 weeks, once every 8 weeks, once every 9 weeks, once every 10 weeks, once every 11 weeks, once every 12 weeks, once every four months, once every five months, once every six months, once every seven months, once every eight months, once every nine months, once every 10 months, once every 11 months, once every 12 months or even less than once a year.

In some aspects, a therapeutically effective amount of the composition is administered. A "therapeutically effective amount" or "therapeutically effective dose" are used interchangeably herein and refer to an amount of a therapeutic agent that provokes a therapeutic or desired response in a subject. In some cases, the therapeutic or desired response is the alleviation of one or more symptoms associated with a disease or disorder. In some cases, a therapeutic or desired response is prophylactic treatment of a disease or a disorder. The pharmaceutical compositions may be administered in a dose that is sufficient to cause a therapeutic benefit to the subject. The dose may vary depending on a variety of factors including the therapeutic agent and the vitreous component binding moiety selected for use. In some cases, a therapeutically effective amount of the conjugated therapeutic agents described herein may be smaller than an unmodified or unconjugated therapeutic agent because the compositions herein may have a longer IVT half-life or mean residence time. In some cases, a composition of the disclosure is administered in quantities that range from about 0.1 mg to about 50 mg in a volume of about 15 µl to about 100 µl per eye.

The compositions described herein may be co-administered with one or more additional therapeutic agents. The one or more additional therapeutic agents may be conjugated to a vitreous component binding moiety as described herein or may be unconjugated. The one or more additional therapeutic agents may be selected from the therapeutic agents described throughout and may enhance or act synergistically in combination with the compositions provided herein.

Indications

The compositions described herein are administered to a subject in need thereof. In some cases, the subject in need thereof is a patient suffering from an ocular disease. In some cases, the ocular disease is a retinal disease. Non-limiting examples of ocular diseases and/or retinal diseases that are amenable to treatment using the compositions and methods described herein include: inflammatory conjunctivitis, including allergic and giant papillary conjunctivitis, macular edema, uveitis, endophthalmitis, scleritis, corneal ulcers, dry eye syndrome, glaucoma, ischemic retinal disease, corneal transplant rejection, complications related to intraocular surgery such intraocular lens implantation and inflammation associated with cataract surgery, Behcet's disease, Stargardt disease, immune complex vasculitis, Fuch's disease, Vogt-Koyanagi-Harada disease, subretinal fibrosis, keratitis, vitreo-retinal inflammation, ocular parasitic infestation/migration, retinitis pigmentosa, cytomegalovirus retinitis, choroidal inflammation, ectropion, lagophthalmos, blepharochalasis, ptosis, xanthelasma of the eyelid, parasitic infestation of the eyelid, dermatitis of the eyelid, dacryoadenitis, epiphora, dysthyroid exophthalmos, conjunctivitis, scleritis, keratitis, corneal ulcer, corneal abrasion, snow blindness, arc eye, Thygeson's superficial punctate keratopathy, corneal neovascularization, Fuchs' dystrophy, keratoconus, keratoconjunctivitis sicca, iritis, uveitis, sympathetic ophthalmia, cataracts, chorioretinal inflammation, focal chorioretinal inflammation, focal chorioretinitis, focal choroiditis, focal retinitis, focal retinochoroiditis, disseminated chorioretinal inflammation, disseminated chorioretinitis, disseminated choroiditis, disseminated retinitis, disseminated retinochoroiditis, exudative retinopathy, posterior cyclitis, pars planitis, Harada's disease, chorioretinal scars, macula scars of posterior pole, solar retinopathy, choroidal degeneration, choroidal atrophy, choroidal sclerosis, angioid streaks, hereditary choroidal dystrophy, choroideremia, choroidal dystrophy (central arealor), gyrate atrophy (choroid), ornithinaemia, choroidal haemorrhage and rupture, choroidal haemorrhage (not otherwise specified), choroidal haemorrhage (expulsive), choroidal detachment, retinoschisis, retinal artery occlusion, retinal vein occlusion, hypertensive retinopathy, diabetic retinopathy, retinopathy, retinopathy of prematurity, macular degeneration, Bull's Eye maculopathy, epiretinal membrane, peripheral retinal degeneration, hereditary retinal dystrophy, retinitis pigmentosa, retinal haemorrhage, separation of retinal layers, central serous retinopathy, retinal detachment, macular edema, glaucoma—optic neuropathy, glaucoma suspect—ocular hypertension, primary open-angle glaucoma, primary angle-closure glaucoma, floaters, Leber's hereditary optic neuropathy, optic disc drusen, strabismus, ophthalmoparesis, progressive external ophthaloplegia, esotropia, exotropia, disorders of refraction and accommodation, hypermetropia, myopia, astigmastism, anisometropia, presbyopia, internal ophthalmoplegia, amblyopia, Leber's congenital amaurosis, scotoma, anopsia, color blindness, achromatopsia, maskun, nyctalopia, blindness, River blindness, micropthalmia, coloboma, red eye, Argyll Robertson pupil, keratomycosis, xerophthalmia, aniridia, sickle cell retinopathy, ocular neovascularization, retinal neovascularization, subretinal neovascularization; rubeosis iritis inflammatory diseases, chronic posterior and pan uveitis, neoplasms, retinoblastoma, pseudoglioma, neovascular glaucoma; neovascularization resulting following a combined vitrectomy-2 and lensectomy, vascular diseases, retinal ischemia, choroidal vascular insufficiency, choroidal thrombosis, neovascularization of the optic nerve, diabetic macular edema, cystoid macular edema, proliferative vitreoretinopathy, and neovascularization due to penetration of the eye or ocular injury.

In some cases, the pharmaceutical compositions can be used to treat retinal diseases. In some cases, the retinal disease is age-related macular degeneration. In some cases, the retinal disease is the exudative ("wet") form of age-related macular degeneration. In some cases, the retinal disease is the non-exudative ("dry") form of age-related macular degeneration. In some cases, the retinal disease is an advanced form of age-related macular degeneration such as geographic atrophy. For example, a pharmaceutical composition for the treatment of geographic atrophy may include a therapeutic agent that targets complement factor D or factor P conjugated to a vitreous component binding moiety.

In some cases, the pharmaceutical compositions can be used to treat diabetic macular edema. In some cases, the pharmaceutical compositions can be used to treat diabetic retinopathy. In some cases, the pharmaceutical compositions can be used to treat retinal vein occlusion. In some cases, the pharmaceutical compositions can be used to treat uveitis.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1. Identification of Aptamers to Hyaluronic Acid (HA)

Standard DNA aptamer selection was conducted against hyaluronic acid (HA), sodium salt (Sigma Aldrich) molecular weight 0.6-1.1 MDa using the DNA library listed in Table 5 (SEQ ID NO. 1). Beginning at round 3 of 12 total rounds of selection, barley-derived β-D-glucan, molecular weight 485 KDa, was used in a pre-clearing step to promote selection of aptamers specific to HA. The selection was conducted in a salt buffer mimicking the vitreous environment, consisting of 10 mM HEPES, pH 7.4, 120 mM NaCl, 5 mM $MgCl_2$ and 5 mM KCl.

TABLE 5

Aptamer Sequences

| SEQ ID NO. | Aptamer Number | Backbone | Sequence (5' to 3') |
|---|---|---|---|
| SEQ ID NO: 1 | Aptamer 1 | DNA | TAGGGAAGAGAAGGACATATGAT (N40)TTGACTAGTACATGACCACTTGA |
| SEQ ID NO: 2 | Aptamer 2 | DNA | TAGGGAAGAGAAGGACATATGATTGG CAAGTATTTGTACATATACTGACGTTT GCCGTACTGCTTGACTAGTACATGACC ACTTGA |
| SEQ ID NO: 3 | Aptamer 3 | DNA | TGGCAAGTATTTGTACATATACTGACG TTTGCCGTACTGC |
| SEQ ID NO: 4 | Aptamer 4 | DNA | TAGGGAAGAGAAGGACATATGATCAC TTCATGTAAGACTAAAAGATGGAGCG TGAAGGATGCATTGACTAGTACATGA CCACTTG |
| SEQ ID NO: 5 | Aptamer 5 | DNA | CACTTCATGTAAGACTAAAAGATGGA GCGTGAAGGATGCA |
| SEQ ID NO: 6 | Aptamer 6 | DNA | TAGGGAAGAGAAGGACATATGATTCC TTTAGAGTGGCGAAGTACCTAATACA ACCTAAAATCCTTGACTAGTACATGAC CACTTGA |
| SEQ ID NO: 7 | Aptamer 7 | DNA | TCCTTTAGAGTGGCGAAGTACCTAATA CAACCTAAAATCC |

Rounds 9 through 12 of the selection were submitted for next-generation sequencing (NGS), and the resultant sequence data was analyzed to identify sequences with the highest rate of enrichment, as defined as the increase in frequency for each sequence from rounds 9 to 10, 10 to 11 and 11 to 12. Sequences that exhibited high rates of enrichment relative to the overall aptamer population included aptamers 2, 4 and 6 listed in Table 5 (SEQ ID NOs 2, 4 and 6).

The affinity of aptamers 2, 4 and 6 for HA, as well as related aptamers 3, 5 and 7 consisting of only the random-region derived portion of these aptamers (SEQ ID NOs 3, 5 and 7), was measured by surface plasmon resonance (SPR). Briefly, biotin-HA (20 KDa) was immobilized on a high-density C7 dextran chip, and aptamer was flowed over the surface with immobilized HA and a control non-HA containing surface at 10° C., at concentrations ranging from 25 µM to 0.39 nM. The HA binding proteins TSG-6 and aggrecan served as controls for specific HA binding in the SPR assay. No resonance above background was observed for aptamers, TSG-6 or aggrecan when flowed over non-HA containing surfaces. The resulting SPR signal for the HA-immobilized surfaces was analyzed assuming a 1:1 binding model, and the affinities for aptamers 2-7 were determined (Table 6). The affinity of aptamers presented in Table 6 for HA may be further improved by reduction in aptamer length, chemical modifications to the 2'position on the deoxyribose, the 5 position of pyrimidine or 8 position of purine nucleotides.

TABLE 6

Affinity of select HA aptamers for HA by SPR analysis

| Aptamer Number | $K_D$ (AVG ± STD) (µM) |
| --- | --- |
| Aptamer 2 | 30 ± 1 |
| Aptamer 3 | 38 ± 1 |
| Aptamer 4 | nd |
| Aptamer 5 | 35 ± 2 |
| Aptamer 6 | 30 ± 2 |
| Aptamer 7 | 38 ± 3 |

Each of the aptamers, with the exception of aptamer 4, bound HA with an apparent affinity ($K_D$) between 30 and 40 µM as determined by SPR. As the selection was conducted with the 5' and 3' fixed regions blocked, it is expected that some full-length sequences may not bind HA, while the aptamers derived from the random region could, which explains the observed binding of aptamer 5 to HA in the absence of apparent HA binding by the full-length sequence from which aptamer 5 was derived.

Example 2. Ocular Retention of HA Aptamers

Treatment of diseases of the posterior segment of the eye require the therapeutic to be retained in the posterior compartment of the eye (i.e. the vitreous humor) at a therapeutic concentration for a sufficient period of time to deliver a useful duration of target suppression with a tolerable dosing interval, while also being able to sufficiently diffuse to the target within the diseased-tissue to provide sufficient target occupancy to provide a therapeutic effect. For retinal diseases, a therapeutic generally must diffuse through the vitreal-retinal interface to access the intended target in the diseased tissue, and depending on the specific indication, may need to penetrate deep into retinal tissue, including reaching the retinal pigment epithelial (RPE) layer to reach the intended target at the site of disease. Retention time or half-life of a drug in the vitreous post-intravitreal administration is a function of clearance of the drug from the vitreous coupled with drug metabolism. For therapeutics with similar rates of metabolism, the clearance rate has the greatest impact on the ability of the therapeutic to achieve a sufficient concentration and half-life (del Amo, E. M, K.-S. Vellonen, H. Kidron, and A. Urtti, 2015, Eur. J. of Pharmaceutics and Biopharmaceutics, 95: 215-226). The rate of clearance from the vitreous is a function of molecular size, with smaller, lower molecular weight molecules clearing more rapidly than higher molecular weight molecules (Shatz, W., P. E. Hass, M. Mathieu, H. S. Kim, K. Leach, M. Zhou, Y. Crawford, A. Shen, K. Wang, D. P. Chang, M. Maia, S. R. Crowell, L. Dickman, J. M Scheer and R. F. Kelley, 2016, Molecular Pharmaceutics, 13:2996-3003). For example, whereas molecules <50 KDa may have a half-life of 3 days or less in the eye in rabbits, those with >80 KDa molecular weight may exhibit a half-life of 6 days or greater in the eye in rabbits (Shatz, W., et. al., 2016).

The ability of a molecule to penetrate the retina and engage targets operating in the retinal tissue is also a function of molecular size, with lower molecular weight molecules exhibiting greater retinal penetration than higher molecular weight molecules (Pitkänen, L., V.-P. Ranta, H. Moilanen, and A. Urtti, 2005, Inv. Ophth and Vis. Sci, 46:641-646). A classic example of this is the comparison of retinal penetration by Fab antibody fragments of a molecular weight of ~50 KDa, which readily penetrate deep into the retinal tissue, effectively reaching the RPE, as compared to a full-length mAb of molecular weight of ~150 KDa, which exhibit poor diffusion in the retina beyond the inner limiting membrane (Mordenti, J., A. Cuthbertson, N. Ferrara, K. Thomsen, L. Berleau, V. Licko, P. C. Allen, C. R., Valverde, Y. G. Meng, D. T. W. Fei, K. M. Fourre, and A. M. Ryan, 1999, Toxicologic Pathology, 27:536-544). Aptamers, with a compact shape and typical molecular weight ranging from 8-15 KDa, are of an ideal molecular weight for retinal penetration, but are rapidly cleared from the vitreous due to their low molecular size and weight. To increase vitreal retention, aptamers may be conjugated to a high molecular weight PEG (e.g. 40 KDa or higher), which due to its large hydrodynamic radius, reduces their clearance rate without greatly compromising their ability to penetrate retinal tissues. PEG does, however, greatly increase the viscosity of a drug formulation, which limits the maximum concentration of drug in a suitable formulation, which, especially given the small volume administrable by intravitreal injection, greatly limits the potential maximum dose administered to the eye due to the limitation viscosity imposes on injectability.

Bispecific aptamers composed of an HA aptamer coupled to a therapeutic aptamer may have a molecular weight of 20 to 30 KDa. Thus, due to their compact size and relatively low molecular weight, such molecules may readily penetrate the retina, but may exhibit a high rate of clearance based solely on their size and molecular weight. However, interaction between aptamers and HA within the vitreous may reduce the rate of diffusion of the aptamer in the vitreous humor, and thus the rate of clearance from the eye following intravitreal administration of said aptamers, as compared to aptamers of similar molecular weight which do not interact with vitreous components. To test this, aptamer No. 5 was synthesized with a 6-carbon amine linker on its 5' end, and labeled with an NHS-activated fluorescent dye-VivoTag®-S 680 (PerkinElmer) to produce a molecule which could be quantified in the eye by fluorescence molecular tomography (FMT). High molecular weight PEG (40 KDa branched PEG) with a terminal amine was similarly labeled with VivoTag®-S 680 to serve as a benchmark for a carrier known to greatly enhance the intravitreal retention of aptamers and related molecules following intravitreal injection.

Rats were distributed into treatment groups of fluorescent dye-labeled aptamer No. 5 or 40 KDa PEG in a manner to maintain the mean body weight in each group within 10% of the overall mean. On the day of treatment, rats were anesthetized with an IP injection of ketamine (80 mg/kg) and xylazine (6 mg/kg). Once fully anesthetized, sterile proparacaine HCl (0.5%) solution was applied topically to both eyes for local anesthesia and analgesia. The rat was positioned so that the eye was visible under an operating microscope. The test article was drawn up with a 33G removable needle attached to a 10 µl glass syringe. The needle was inserted just above the ciliary body at a 45-degree angle to the sclera. Rats were administered a single intravitreal injection to right and left eyes at a dose of test article ranging from 0.2 to 2 nmole based on the VivoTag®-S 680 dye concentration at an intravitreal dosing volume of 3 µl total volume. After injection, the needle was removed and a cotton tip swab was used to absorb any leakage.

Retention in the eye over time following a single intravitreal injection was evaluated using fluorescence molecular tomography (FMT). This approach enables the calculation of the percent dose remaining in each treated eye over time by making serial FMT measurements and normalizing fluorescent intensity of the area of interest to that measured at 0 to 5 minutes post-test article administration for each treated eye. In vivo FMT was performed on the Perkin-Elmer FMT 2500™ LX Quantitative Tomography Imaging System (PerkinElmer, Hopkinton, Mass.). Just prior to imaging, the rats were anesthetized using 2% isoflurane gas anesthesia in air, and maintained under 2% isoflurane throughout the imaging session. The anesthetized rats were placed into the imaging cassette in the lateral position, ensuring that the eye was located within the scan field of the imaging system. Each rat was positioned laterally on the left side to image the right eye and laterally on the right side to image the left eye. The imaging cassette was then inserted into the heated docking system (regulated at 37° C.) in the FMT imaging chamber. Each rat was maintained under 2% isoflurane anesthesia throughout the imaging session. A scanning region was manually positioned over the subject head prior to the fluorescence scan. The laser power and exposure time at each scan point were automatically adjusted by the system to provide high signal to noise while avoiding saturation. Total scan times were on the order of 2-4 minutes for each scan. During the scan, images of the trans-illuminated animal were captured at both the excitation and fluorescent wavelengths for each source position. Quantification accuracy of the FMT system was assessed with a near-infrared dye (VivoTag®-S680).

The collected fluorescence data images were reconstructed by the FMT system software (TruQuant™; PerkinElmer) for the quantification of the fluorescence signal within the eyes. Three-dimensional regions of interest (ROIs) were drawn around the eye. The total amount (in picomole) of fluorochrome was automatically calculated relative to internal standards generated with known concentrations of the appropriate fluorochrome. For each study, the mean fluorescence at time 0 or 5 minutes post-dose was equaled to 100% and then each rat within a study was normalized accordingly.

The retention of aptamer No. 5 compared to PEG at time 0 and 48 hours post administration of a 0.8 nmole dose of each test article is shown in Table 7. The 48-hour time-point was chosen as the comparator time point because it provides a substantial clearance window at which the remaining PEG concentration was reliably quantifiable above the lower limit of quantitation for the imaging system. As shown in Table 7, HA-binding by aptamer No. 5 provided a retention of the administered intravitreous dose comparable to 40 KDa PEG, demonstrating the binding of the aptamer to HA increased its retention time in the vitreous comparable to that of the much larger, higher molecular weight PEG carrier molecule. It is anticipated that the intravitreal retention of aptamer No. 5 can be further improved by increasing its metabolic stability, by for example, substitution of DNA nucleotides for 2'Omethyl or 2'fluoro nucleotides, or introduction of backbone modifications such as phosphorothioates and di-thioates. Yet further improvement of the intravitreal retention of aptamer No. 5 may be obtained by chemical substitutions to increase its affinity for HA, such as described in Example 1.

TABLE 7

Retention of HA aptamer at 48 hrs post-injection compared to 40 KDa PEG

| Compound | Mean % Remaining Dose ± STD | |
|---|---|---|
| | 0 hrs | 48 hrs |
| 40 KDa S680-labeled PEG | 100 | 4.2 ± 1.4 |
| Aptamer 5 S680-labeled | 100 | 3.4 ± 2.0 |

Example 3. Bi-Specific HA-PDGF Aptamers

The Examples herein describe assays that determine the activity of molecules that both bind and inhibit a protein with biologic activity, for example proteins such as growth factors, and also bind to a vitreous extracellular matrix component, for example HA. For example, the molecules may be small molecules, proteins or nucleic acids. In some examples, the molecules are nucleic acids that form a tertiary structure that can directly bind PDGF and inhibit PDGF activation of cell proliferation, and also directly bind HA.

In one example, the two activities are present on a contiguous nucleic acid sequence that is synthesized in a manner resulting in two tethered tertiary structures that bind PDGF and HA. In another example, the two activities are present in two separate nucleic acid sequences that are independently synthesized and then chemically linked in a manner that results in two tethered tertiary structures that bind PDGF and HA.

The disclosure provides for identification of platelet-derived growth factor-B (PDGF-B) inhibitors in a PDGF-dependent cell proliferation assay. An anti-PDGF aptamer (SEQ. ID NOs: 8, 17, and 18, Table 8) was developed that directly binds to and selectively inhibits PDGF-B activity (Floege J. T. Ostendorf, U. Janssen, M. Burg, H H Radeke, C. Vargeese, S C Gill, L. S. Green and N. Janjic, 1999, Am. J. Pathol 154:169-179). In one example, the anti-PDGF binding aptamer is synthesized by solid phase oligonucleotide synthesis followed by a hexaethylene spacer as a linker and then the HA aptamer, thereby producing an HA-PDGF bispecific aptamer that can tether the anti-PDGF aptamer to HA within the vitreous to produce a therapeutic with low vitreal clearance and thereby enhanced vitreous half-life following intravitreal administration.

TABLE 8

Aptamer Sequences

| SEQ ID NO. | Aptamer Number | Backbone | Sequence (5' to 3') |
|---|---|---|---|
| SEQ ID NOs: 8 17, and 18 | Aptamer 8 | DNA/ RNA | C6NH2CAGGCfUAfCmG[ISp18]CGTA mGAmGCAfUfCmA[ISp18]TGATfCfCf UmGidT |
| SEQ ID NOs: 9 and 19-21 | Aptamer 9 | DNA/ RNA | TGGCAAGTATTTGTACATATACTGA CGTTTGCCGTACTGC[ISp18]CAGGCf UAfCmG[ISp18]CGTAmGAmGCAfUfC mA[ISp18]TGATfCfCfUmGidT |
| SEQ ID NOs: 10, 22, and 23 | Aptamer 10 | DNA/ RNA | CACTTCATGTAAGACTAAAAGATG GAGCGTGAAGGATGCACAGGCfUAf CmG[ISp18]CGTAmGAmGCAfUfCmA [ISp18]TGATfCfCfUmGidT |
| SEQ ID NOs: 11, 24, and 25 | Aptamer 11 | DNA/ RNA | TCCTTTAGAGTGGCGAAGTACCTA ATACAACCTAAAATCCCAGGCfUAf CmG[ISp18]CGTAmGAmGCAfUfCmA [ISp18]TGATfCfCfUmGidT |

Where [ISp18] is an 18 atom hexaethylene glycol spacer; mG or mA is 2'Omethyl RNA; fC or fU is 2'fluoro RNA; idT is inverted deoxythymidine Three examples of aptamers that contain an HA binding module followed by an anti-PDGF module are aptamer Nos. 9 (SEQ ID NOs: 9, and 19-21), 10 (SEQ ID NOs: 10, 22, and 23) and 11 (SEQ ID NOs: 11, 24, and 25), which include, respectively, bispecifics of aptamer Nos. 3, 5 and 7 combined with aptamer No. 8 (Table 8). To determine whether these aptamers with tethered second domains retained PDGF-B activity, they were compared to aptamer No. 8 for the ability to inhibit PDGF-B stimulated cell proliferation (FIG. 1). Aptamer Nos. 9, 10 and 11 all retained PDGF-B inhibitory activity similar to aptamer No. 8.

Stimulation of cell proliferation by PDGF-B (R&D Systems 220-BB) in the mouse 3T3 cell line (ATCC CRL-1658) was quantified through the reduction of MTT (Roche 11-465-007-001) into Formozan by mitochondrial succinate dehydrogenase in live cells. Flat bottom 96-well plates were seeded with 15,000 3T3 cells/well in 100 µL DMEM/10% FBS and incubated overnight at 37° C. with 5% $CO_2$. The cell medium was replaced with 90 µL pre-warmed DMEM/0.8% FBS and cells were incubated for 3 hours at 37° C. 5 µL aptamers were mixed with 5 µL PDGF-B to yield a final PDGF-B concentration of 2 nM, and final aptamer concentrations of 80, 40, 20, 10, 5, 2.5, 1.25, 0.625 or 0 µM, and added to the 90 µL medium in each well. Cells were incubated at 37° C. with 5% $CO_2$ for 3 days, then 10 µL MTT solution was added and incubated for a further 1.5 hours at 37° C. with 5% $CO_2$. Media was then removed and 200 µL of 100% isopropanol was added to each well, then Formozan formation was quantified through its optical absorbance at 570 nm.

The disclosure provides for identification of molecules that bind HA as determined by competing with Tumor necrosis factor-stimulated gene-6 (TSG-6) binding to HA in a TR-FRET assay. TSG-6 is a protein that binds HA via the Link module of TSG-6 (Higman, V. A., D. C. Briggs, D. J. Mahoney, C. D Blundell, B. M. Sattelle, D. P. Dyer, D. E. Green. P. L DeAngelis, A. Almond, C. M. Milner and A. J. Day, 2014, J. Biol. Chem. 289:5619-5634.). TSG-6 binds optimally to an octasaccharide unit of HA, which is a high molecular weight extracellular matrix polysaccharide that consists of repeating disaccharides of D-glucuronic acid and N-acetyl-D-glucosamine (Higman et al., 2014).

Binding of 10×-His-TSG6 to 20 KDa mono-biotinylated HA is detected through time-resolved fluorescent resonance energy transfer (TR-FRET) or homogenous time resolved fluorescence (HTRF) using Mab Anti 6His-Tb cryptate Gold ("6×His" disclosed as SEQ ID NO:27) (Cisbio #61H12TLA) and Streptavidin-XLent (Cisbio #611SAXLA). When the Tb cryptate tagged anti-his antibody binds to 10×-His-TSG6, and XLent-tagged streptavidin binds to biotinylated HA, the proximity of the Xlent donor to the Tb cryptate acceptor results in higher HTRF signal. This signal is measured at two wavelengths, 620 nm donor fluorescence and 665 nm accepter fluorescence, and the ratio of the fluorescence of the acceptor over that of the donor is calculated to determine the relative amount of complex formed. This HTRF signal is proportional to the amount of TSG-6 that binds HA, and non-His tagged molecules that compete for TSG-6 binding to HA cause a decrease in the HTRF signal.

In flat bottom 384-well plates the following reagents are added in PBS buffer pH 7.4 (10 mM phosphate buffer, 137.5 mM NaCl, 5.7 mM KCl, 1 mM $MgCl_2$, 1 mM $CaCl_2$, 0.1% BSA and 0.05% Tween): Anti 6×His-Tb cryptate Gold ("6×His" disclosed as SEQ ID NO:27)+TSG6+Mono-Biotin Labeled Hyaluronan+up to 125 μM aptamer, for a total volume of 15 μL. After incubating at room temperature for 30 minutes, Streptavidin-XLent is added and the HTRF signal is read at 665/620 nm.

In one aspect, a nucleic acid that adopts a conformation that binds HA sterically inhibits TSG-6 from concurrently binding to the same HA molecule, resulting in a decreased HTRF signal. Exemplary modified nucleic acid sequences that bind HA are aptamer Nos. 9, 10 and 11 which at 125 μM decrease TSG-6 binding to HA to 30, 32, and 27% respectively (Table 9 and FIG. 2).

TABLE 9

| Inhibition of HA-binding by HA-PDGF bispecific aptamers | | | |
|---|---|---|---|
| Aptamer | No. 9 | No. 10 | No. 11 |
| HA-binding Activity (%) | 30 | 32 | 27 |

Aptamer Nos. 9, 10 and 11 are bispecific molecules possessing a PDGF inhibitory domain and an HA binding domain. Given the increased intravitreal retention exhibited by aptamer No. 5 in Example 2, aptamer Nos. 9, 10 and 11 are HA-PDGF bispecific aptamers anticipated to exhibit increased retention in the vitreous relative to molecules of comparable molecular weight, and thus a prolonged intravitreal half-life and duration of PDGF inhibitory effect.

Example 4. Evaluation of HA-PDGF and VEGF Bispecific Aptamer Duration of Effect in Rodent Challenge Models The duration of action of HA-therapeutic bispecific aptamers can be evaluated in rodent challenge models. In this example, a rat PDGF-BB challenge model and a rat VEGF challenge model were used to evaluate the efficacy of HA-PDGFB molecules or HA-VEGF bispecific aptamers to decrease or prevent vascular vessels leakage induced by the intravitreal (IVT) administration of PDGF-BB or VEGF, respectively, into the rat's eyes. The eye vascular vessel leakage concentration and time responses following PDGF-BB or VEGF induced vascular vessel leakage were quantified by fluorescein angiograms (FA) and Evans blue leakage (EB) assays. For the PDGF-BB challenge model, the IVT administration of PDGF-BB at 30 ng/eye induced vessels leakage in the eyes. For the VEGF challenge model, the IVT administration of VEGF at 1 ng/eye induced vessels leakage in the eyes. Vascular vessel leakage in the eyes was as evaluated by fluorescein angiograms and Evans blue leakage assays. In these studies, the duration of effect of the therapeutic can be determined by administration of the HA-therapeutic bispecific aptamer at different days prior to administration of the PDGF-BB or VEGF challenge. For example, the HA-therapeutic bispecific aptamer can be administered 3, 7, 14, 21 or 28 days prior to the challenge to evaluate whether an effective amount of the therapeutic remains in the eye at the time the growth factor challenge is administered. Comparison groups using pegylated and nonconjugated versions of the therapeutic aptamer can also be included to demonstrate the increased duration of action when the therapeutic aptamer is conjugated to an HA aptamer.

In this example, to validate the PDGF-BB and VEGF challenge models, a pilot study was conducted using pegylated aptamer No. 8 to determine the dependence of vascular leakage on PDGF-BB activity, and an anti-VEGF Fab was used to determine the dependence of vascular leakage on VEGF therapy, with each agent being tested alone, and in combination. Rats were anesthetized with ketamine/xylazine (~75 mg/kg:10 mg/kg) and pegylated aptamer No. 8 (73 µg in 3 µL), or anti-VEGF therapy (10 µg in 1 µL), or pegylated aptamer No. 8 and anti-VEGF therapy, or saline/PBS were administered to rats left and right eye intravitreally. For groups receiving monotherapy, a second PBS injection of 1 or 3 µL was administered to account for multiple injections in the PDGF+VEGF treatment group. On day 3, vascular leakage was induced with 1 µL of 30 ng/µL PDGF-BB, or 1 ng/µL VEGF-A121 (1 µL) or 1 µL of saline. Intravitreal injections were conducted under a microscope using a 10 or 25 µL Hamilton syringes with a 30 gauge needle.

Figure 3:
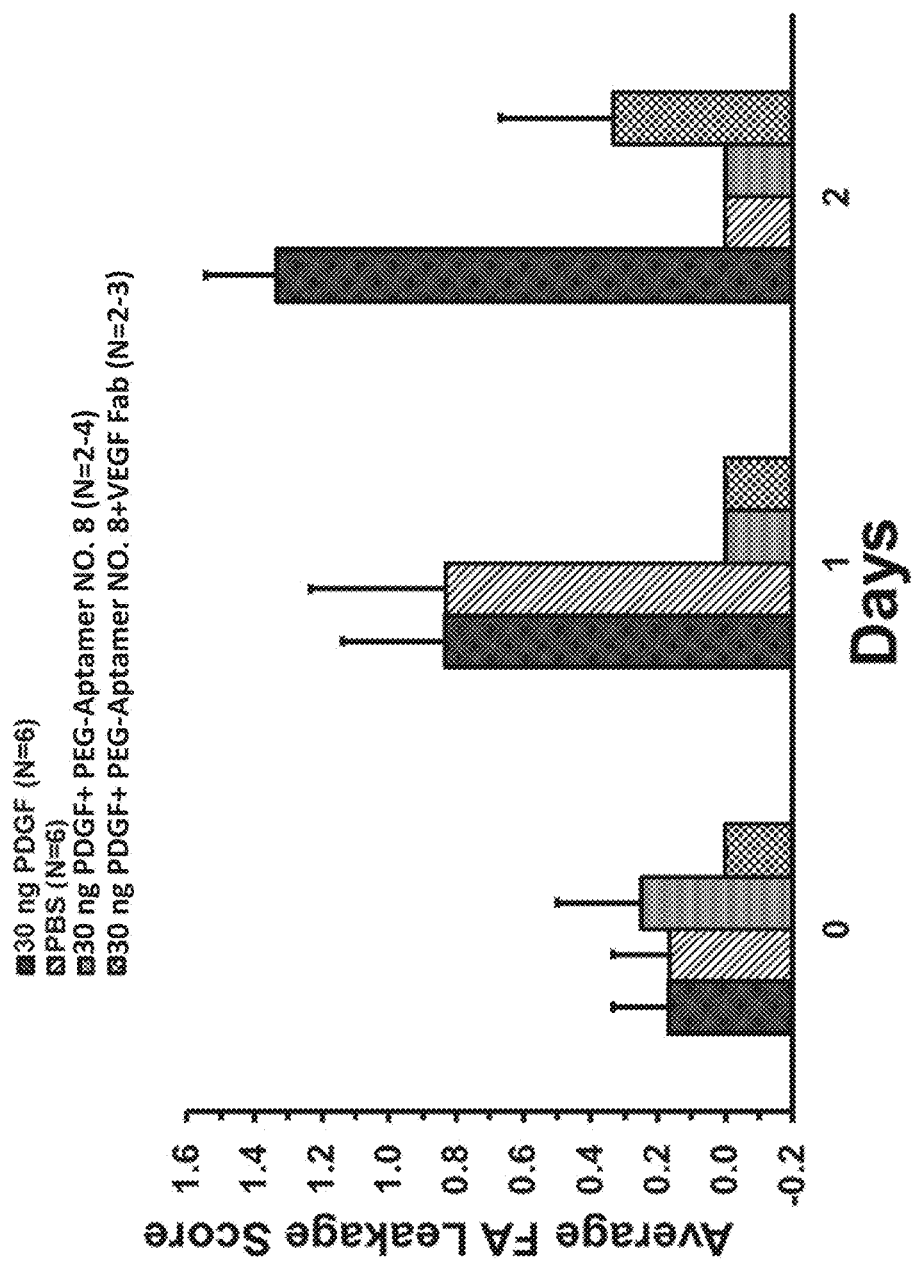
FIG. 3 depicts inhibition of vascular leakage induced by PDGFB challenge by treatment with pegylated aptamer No. 8 separately or in combination with anti-VEGF mAb as measured by fluorescein angiography.
Figure 4:
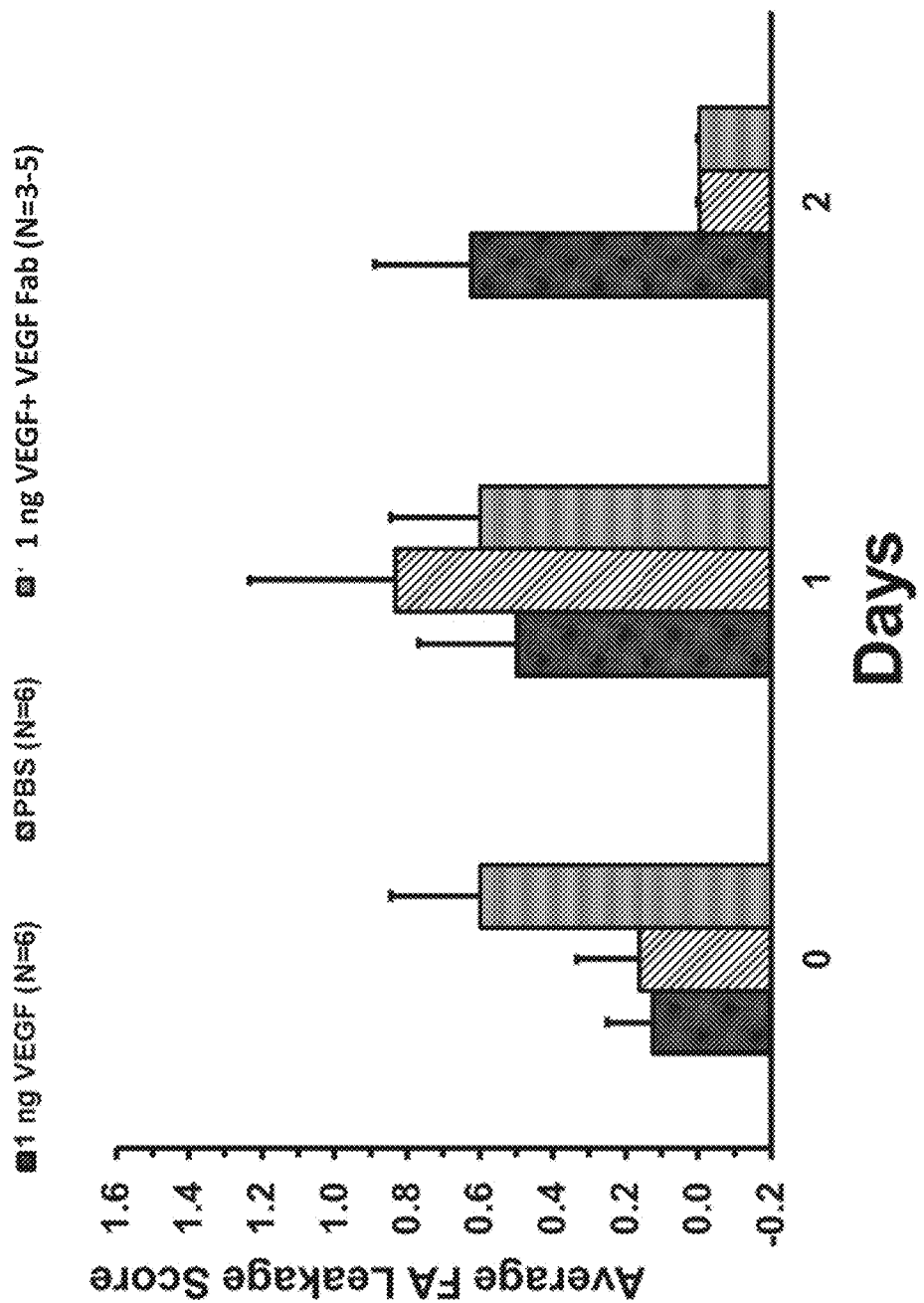
FIG. 4 depicts inhibition of vascular leakage induced by VEGF challenge by treatment with anti-VEGF mAb as measured by fluorescein angiography.

Vascular leakage was evaluated by fluorescein angiography (FA). Fluorescein angiography was performed immediately before administration of test articles or PBS, immediately before PDGF-BB or VEGF dosing, and at 24, 48, 72, and 96 h post-dose. For qualitative fluorescein leakage scoring, animals were anesthetized with ketamine/xylazine (~75 mg/kg:10 mg/kg) and then they were administered 0.5 mL/kg 10% Na-fluorescein intraperitoneally to visualize the retinal vasculature. Photographs and videos of the retinas were recorded with the Micron III fundus camera at 1-6 minutes post injection to record and score both early and late phase angiograms. Image assessment was randomized and masked images were scored for leakage accordingly: Score 0—no signs of leakage from the retinal vessels; Score 1—a haze suggestive of fluorescence leakage from retinal vessels; If the perceived leakage is subtle, an increase in tortuosity can be used to confirm a score of 1; Score 2—unambiguous fluorescein leakage over most or all of the retinal vessels. FA leakage score was determined as the difference of early and late individual FA scores. As shown in FIG. 3, administration of pegylated aptamer No. 8 alone or in combination with anti-VEGF therapy reduced vascular leakage as measured by FA, verifying the dependence of vascular leakage on PDGF activity in this model. Likewise, as shown in FIG. 4, administration of anti-VEGF therapy reduced vascular leakage as measured by FA, verifying the dependence of vascular leakage on VEGF activity in this model.

Figure 5:
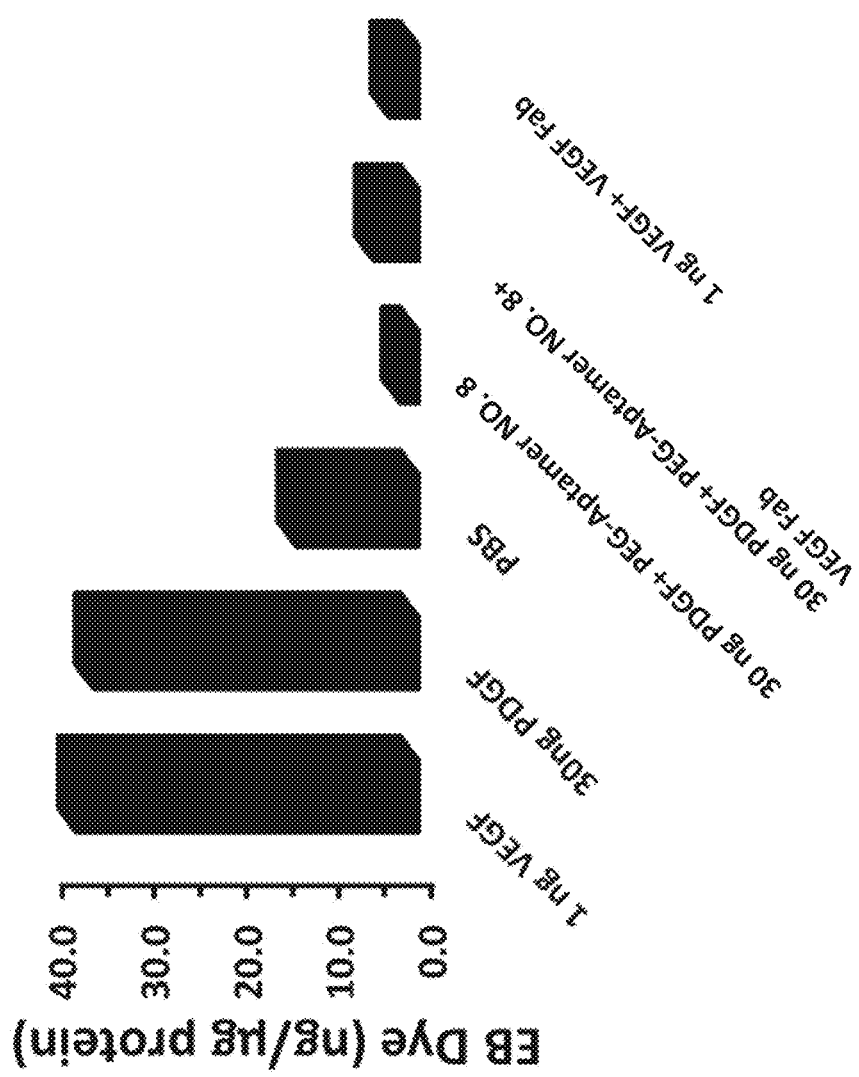
FIG. 5 depicts inhibition of vascular leakage induced by PDGFB or VEGF challenge by treatment with pegylated aptamer No. 8 and anti-VEGF mAb administered separately or in combination as measured by Evan's Blue (EB).

Evans Blue (EB) dye covalently links to albumin and serves as a sensitive quantitative indicator of albumin leakage into the retina from the vasculature. Under deep anesthesia, EB in sterile heparinized saline was injected intravenously (30 mg/mL; 30 mg/kg) through the tail vein. After 1 hour, EB was washed out through perfusion of the vasculature using 1% paraformaldehyde in sterile heparinized citric buffer (pH 3.5), pre-warmed to 37° C., using gentle syringe perfusion, the eyes were enucleated, and the retina removed. EB content was determined by spectrophotometry following dye extraction. As shown in FIG. 5, treatment with pegylated aptamer No. 8 alone or in combination with anti-VEGF therapy as well as anti-VEGF therapy alone quantitatively reduced vascular leakage induced by PDGF-BB or VEGF, further demonstrating the dependence of vascular leakage in this model on the respective PDGF-BB and VEGF activity.

The ability of HA aptamers to increase the duration of the therapeutic effect of therapeutic aptamers is demonstrated using the rat PDGF-BB challenge model. Rats are assigned to treatment with pegylated aptamer No. 8 (75 µg in 3 µL), or the HA-PDGF bispecific aptamer No. 9 (75 µg in 3 µL) or PBS. For each treatment, groups of rats are treated with pegylated aptamer No. 8 or aptamer No. 9 or PBS at 28, 21, 14, 7 or 3 days prior to administration of 30 ng PDGF-BB. Vascular leakage is then determined as described above. For groups treated 3 days prior to PDGF-BB challenge, pegylated aptamer No. 8 and No. 9 show comparable efficacy. For groups treated at days 7 or 14, aptamer No. 9 shows a significantly greater therapeutic effect than animals treated with pegylated aptamer No. 8, demonstrating the increased duration of therapeutic effect provided by conjugation of the therapeutic aptamer to an HA aptamer as compared to conjugation to PEG. Likewise, some therapeutic effect of aptamer No. 9 persists in the 21 and 28 day dose groups, compared to no therapeutic effect of pegylated aptamer No. 8.

The ability of HA aptamers to increase the duration of the therapeutic effect of therapeutic aptamers is demonstrated using the rat VEGF challenge model. Rats are assigned to treatment with pegylated aptamer No. 12 (5 µg in 3 µL), or the HA-VEGF bispecific aptamer No. 13 (5 µg in 3 µL) or PBS. For each treatment, groups of rats are treated with pegylated aptamer No. 12 or aptamer No. 13 or PBS at 28, 21, 14, 7 or 3 days prior to administration of 1 ng VEGF- A165. Vascular leakage is then determined as described above. For groups treated 3 days prior to VEGF challenge, pegylated aptamer No. 12 and No. 13 show comparable efficacy. For groups treated at days 7 or 14, aptamer No. 13 shows a significantly greater therapeutic effect than animals treated with pegylated aptamer No. 12, demonstrating the increased duration of therapeutic effect provided by conjugation of the therapeutic aptamer to an HA aptamer as compared to conjugation to PEG. Likewise, some therapeutic effect of aptamer No. 13 persists in the 21 and 28 day dose groups, compared to no therapeutic effect of pegylated aptamer No. 12.

Example 5. Treatment of Wet Age-Related Macular Degeneration (wAMD) with HA-PDGF Bispecific Aptamers Aptamer No. 8 conjugated to 40 KDa PEG (E10030) is an anti-PDGF-B aptamer with demonstrated potent inhibition of PDGF and clinical efficacy in phase 2 studies for the treatment of wet age-related macular degeneration (wAMD) in combination with anti-VEGF therapy. However, in phase 3 studies for the treatment of wAMD, E10030 when added to anti-VEGF standard of care failed to show an improvement over anti-VEGF standard of care alone. In this example, aptamer No. 8, the aptamer component of E10030 is tethered to aptamer No. 3 by solid phase synthesis to produce a bispecific aptamer consisting of an HA-binding domain and a PDGF inhibitor domain to yield aptamer No. 9, which has a molecular weight of approximately 22,750 Da (Table 8). Alternatively, aptamer No. 3 is produced with a C6-disulfide linker, and is conjugated to aptamer No. 8 by first reacting aptamer No. 8 with a maleimide-$PEG_8$-NHS linker, followed by reduction of the disulfide on aptamer No. 3 and reaction with the maleimide-$PEG_8$-C6-aptamer No. 8 to produce a bispecific construct consisting of the 5' end of aptamer No. 3 tethered to the 5' end of aptamer No. 8 via a $PEG_8$ linker.

E10030 is presented as an isotonic, neutral pH formulation at a concentration of 30 mg/mL based on oligonucleotide molecular weight and is administered intravitreally via a 27-gauge needle at a 50 µL volume for a maximum dose of 1.5 mg/eye. The maximum dose of E10030 is limited by the viscosity of the drug product solution to 1.5 mg in a 50 µL volume of injection via a 27-gauge needle. Use of higher gauge needles with E10030 would further reduce the maximum administrable dose. By contrast, in one embodiment, aptamer No. 9 is presented at a concentration of 100 mg/ml in a prefilled syringe administrable via a 27-33 gauge needle for a dose of 5 mg in a 50 µL volume of injection. The dynamic viscosity of a dosage form (or concentration) provided herein may be about 38,800 centipoise to about 194,100 centipoise, about 97,000 centipoise to about 485,500 centipoise, or about 194,100 centipoise to about 970,800 centipoise when formulated in a 50 µL pre-filled syringe with a ½ inch 27-gauge needle. The dynamic viscosity of a dosage form (or concentration) provided herein may be about 13,100 centipoise to about 65,000 centipoise, about 32,700 centipoise to about 164,000 centipoise, or about 65,000 centipoise to about 325,000 centipoise when formulated in a 50 µL pre-filled syringe with a ½ inch 30-gauge needle. Similarly, the dynamic viscosity of a dosage form (or concentration) provided herein may be about 2,800 centipoise to about 14,500 centipoise, about 7,300 centipoise to about 36,500 centipoise, or about 14,500 to about 75,000 centipoise when formulated in a 50 µL pre-filled syringe with a ½ inch 33-gauge needle. In another embodiment, given the lower viscosity of aptamer No. 9 relative to E10030, it is anticipated that presentations of 200 to 250 mg/ml or greater would possess a sufficiently low viscosity to be administered in a 27-33 gauge needle to provide a dose of 10 to 15 mg or greater in a 50 µL volume of injection. In general, aptamers conjugated to an HA aptamer binding module are formulated either in dilute phosphate buffer (for example, in the range of 5 to 10 mM phosphate) at or near pH 7.4, or in pure water adjusted to or near pH 7.4. Additives, including buffering salts, may be used sparingly, if at all, according to a recent publication from USP and the FDA.

The presentation of a therapeutic aptamer such as the aptamer No. 9 is anticipated to provide a favorable presentation for intravitreal administration compared to the same aptamer conjugated to a high molecular weight PEG, such as a branched 40 KDa PEG used for Macugen®, Fovista® and Zimura®. While conjugation of PEG to an aptamer confers the desired effect of extending intravitreal half-life, it also contributes substantially to the viscosity of the solution. PEG is a well-known shear thickener, meaning that the viscosity of a solution of given concentration is not a fixed parameter, but increases with increased shear force applied to the solution. This phenomenon leads to serious limitations in the administration of PEGylated aptamers because a compromise must be achieved between concentration of dosing solution and the diameter of the needle used to administer the drug. Conjugation of a therapeutic aptamer to an HA aptamer (HA-therapeutic aptamer bispecifics) presents the opportunity to achieve the requisite clinical concentration of drug product without encountering shear thickening. In addition, the lower overall size and molecular weight of the HA-therapeutic aptamer bispecific is only about 40% of the aptamer conjugated to a 40-kilodalton PEG. Thus, an HA-therapeutic aptamer bispecific is anticipated to be a more compact structure than the comparable PEGylated aptamer, leading to less intermolecular interaction. HA-therapeutic aptamer bispecific clinical products are more likely to achieve the requisite clinical concentration at a viscosity that permits administration via a needle of gauge 28, 30, or even 33. Thus, discomfort to the patient is minimized as is the risk of serious injury during administration.

Aptamer No. 9 can be administered to patients with wAMD at a dose of 5 to 15 mg/eye using the formulation described above via a pre-filled syringe consisting of 50 µL for injection with a ½ inch 30-33 gauge needle. Aptamer No. 9 may be administered in combination with anti-VEGF therapy, which may consist of either 1.25 mg of Avastin®, 0.5 mg of Lucentis® or 2 mg of Eylea®, the injections of which can be performed independently.

Aptamer No. 9 is anticipated to have a half-life of 10 to 28 days in the vitreous to support administration every 3 to 6 months, whereas anti-VEGF therapy can be administered every 1 or 2 months based on the package insert for the selected anti-VEGF therapy.

Administration of aptamer No. 9 in combination with anti-VEGF therapy is anticipated to improve the mean change in visual acuity (ETDRS letters) from baseline by 12 months of therapy. Administration of aptamer No. 9 in combination with anti-VEGF therapy can be monitored for adverse events, including changes in ophthalmic examinations, intraocular pressure, fluorescein angiography, optical coherence tomography, ECG and laboratory variables. Overall, the combination of aptamer No. 9 with anti-VEGF therapy is anticipated to be more efficacious than the combination therapy of E10030 with anti-VEGF therapy because of the increased dose of anti-PDGFB therapeutic administered. Further, given the longer duration of effect of aptamer No. 9 compared to E10030, it is also anticipated that treatment with aptamer No. 9 can result in fewer side effects given the lower number of injections with a higher gauge needle over the treatment period.

Example 6. Treatment of wAMD with HA-VEGF Bispecific Aptamers

Aptamer No. 12 (Ruckman, J., L. S. Green, J. Beeson, S. Waugh, W. L. Gillette, D. D. Henninger, L. Claesson-Welsh, and N. Janjic, 1998, J. Biol. Chem. 273:20556-20567) conjugated to 40 KDa PEG (NX1838, Macugen®) is an anti-VEGF aptamer that binds to the heparin-binding domain of VEGF with demonstrated potent inhibition of VEGF and clinical efficacy in the treatment of wet age-related macular degeneration (wAMD). In this example, the aptamer component of NX1838 (aptamer No. 12) is tethered to aptamer No. 5 by solid phase synthesis to produce a bispecific aptamer consisting of an HA-binding domain and a VEGF inhibitor domain to yield aptamer No. 13, which has a molecular weight of approximately 22,100 Da (Table 10). Alternatively, aptamer No. 5 is produced with a C6-disulfide linker, and is conjugated to aptamer No. 12 by first reacting aptamer No. 12 with a maleimide-$PEG_8$-NHS linker, followed by reduction of the disulfide on aptamer No. 5 and reaction with the maleimide-$PEG_8$-C6-aptamer No. 12 to produce a bispecific construct consisting of the 5' end of aptamer No. 5 tethered to the 5' end of aptamer No. 12 via a $PEG_8$ linker.

centration) provided herein may be about 13,100 centipoise to about 65,000 centipoise, about 32,700 centipoise to about 164,000 centipoise, or about 65,000 centipoise to about 325,000 centipoise when formulated in a 50 μL pre-filled syringe with a ½ inch 30-gauge needle. Similarly, the dynamic viscosity of a dosage form (or concentration) provided herein may be about 2,800 centipoise to about 14,500 centipoise, about 7,300 centipoise to about 36,500 centipoise, or about 14,500 to about 75,000 centipoise when formulated in a 50 μL pre-filled syringe with a ½ inch 33-gauge needle.

In another embodiment, given the lower viscosity of aptamer No. 13 relative to pegaptinib, it is anticipated that presentations of 200 to 250 mg/ml or greater would possess a sufficiently low viscosity to be administered in a 27-33 gauge needle to provide a dose of 10 to 15 mg or greater in a 50 μL volume of injection.

In general, aptamers conjugated to an HA aptamer binding module may be formulated either in dilute phosphate buffer (for example, in the range of 5 to 10 mM phosphate) at or near pH 7.4, or in pure water adjusted to or near pH 7.4. Additives, including buffering salts, will be used sparingly, if at all, according to a recent publication from USP and the FDA.

The presentation of a therapeutic aptamer such as the aptamer No. 12 conjugated to an HA aptamer is anticipated to provide a favorable presentation for intravitreal administration compared to the same aptamer conjugated to a high molecular weight PEG, such as a branched 40 KDa PEG used for Macugen®, Fovista® and Zimura®. While conju-

TABLE 10

Aptamer Sequences

| SEQ ID NO: | Aptamer Number | Backbone | Sequence (5' to 3') |
| --- | --- | --- | --- |
| SEQ ID NO: 12 | Aptamer 12 | RNA | C6NH2fCmGmGrArAfUfCmAmGfUm GmAmAfUmGfCfUfUmAfUmAfCmA fUfCfCmGidT |
| SEQ ID NOs: 13 and 16 | Aptamer 13 | DNA/ RNA | CACTTCATGTAAGACTAAAAGAT GGAGCGTGAAGGATGCA[ISp18]fC mGmGrArAfUfCmAmGfUmGmAmAf UmGfCfUfUmAfUmAfCmAfUfCfCm GidT |

Where [ISp18] is an 18 atom hexaethylene glycol spacer; mG or mA is 2'Omethyl RNA; fC or fU is 2'fluoro RNA; rG or rA is 2'OH RNA; idT is inverted deoxythymidine Macugen® is presented as an isotonic, neutral pH formulation at a concentration of 3.5 mg/mL based on oligonucleotide molecular weight and is administered intravitreally via a 30-gauge ½ inch long needle at a 90 μL volume for a maximum dose of 0.3 mg/eye. The maximum dose of Macugen® is limited by the viscosity of the drug product solution to 0.3 mg in a 90 μL volume of injection via a 30-gauge needle. Use of higher gauge needles with pegaptanib would further reduce the maximum administrable dose. By contrast, in one embodiment, aptamer No. 13 is presented at a concentration of 100 mg/mL in a prefilled syringe administrable via a 27-33 gauge needle for a dose of 5 mg in a 50 μL volume of injection. The dynamic viscosity of a dosage form (or concentration) provided herein may be about 38,800 centipoise to about 194,100 centipoise, about 97,000 centipoise to about 485,500 centipoise, or about 194,100 centipoise to about 970,800 centipoise when formulated in a 50 μL pre-filled syringe with a ½ inch 27-gauge needle. The dynamic viscosity of a dosage form (or congation of PEG to an aptamer confers the desired effect of extending intravitreal half-life, it also contributes substantially to the viscosity of the solution. PEG is a well-known shear thickener, meaning that the viscosity of a solution of given concentration is not a fixed parameter, but increases with increased shear force applied to the solution. This phenomenon leads to serious limitations in the administration of PEGylated aptamers because a compromise must be achieved between concentration of dosing solution and the diameter of the needle used to administer the drug. Conjugation of therapeutic aptamer to HA aptamers (HA-therapeutic aptamer bispecifics) presents the opportunity to achieve the requisite clinical concentration of drug product without encountering shear thickening. In addition, the lower overall size and molecular weight of the HA-therapeutic aptamer bispecific is only about 40% of the aptamer conjugated to a 40-kilodalton PEG. Thus, an HA-therapeutic aptamer bispecific is anticipated to be a more compact structure than the comparable PEGylated aptamer, leading to less intermolecular interaction. HA-therapeutic aptamer bispecific clinical products are more likely to achieve the requisite clinical concentration at a viscosity that permits administration via a needle of gauge 28, 30, or even 33. Thus, discomfort to the patient is minimized as is the risk of serious injury during administration.

gated to aptamer No. 14 by first reacting aptamer No. 14 with a maleimide-$PEG_8$-NHS linker, followed by reduction of the disulfide on aptamer No. 7 and reaction with the maleimide-$PEG_8$-C6-aptamer NO. 14 to produce a bispecific construct consisting of the 5' end of aptamer No. 7 tethered to the 5' end of aptamer No. 14 via a $PEG_8$ linker.

TABLE 11

Aptamers Sequences

| SEQ ID NO. | Aptamer Number | Backbone | Sequence (5' to 3') |
|---|---|---|---|
| SEQ ID NO: 14 | Aptamer 14 | RNA | C6NH$_2$fCmGfCfCrGfCmGmGfUfCf UfCmAmGmGfCrGfCfUmGmAmGf UfCfUmGmAmGfUfUfUrAfCfCfUm GfCmGidT |
| SEQ ID NOs: 15 and 26 | Aptamer 15 | DNA/ RNA | TCCTTTAGAGTGGCGAAGTACC TAATACAACCTAAAATCC[ISp18] fCmGfCfCrGfCmGmGfUfCfUfCmA mGmGfCrGfCfUmGmAmGfUfCfU mGmAmGfUfUfUrAfCfCfUmGfCm GidT |

Where [ISp18] is an 18 atom hexaethylene glycol spacer; mG or mA is 2'Omethyl RNA; fC or fU is 2'fluoro RNA; rG or rA is 2'OH RNA; idT is inverted deoxythymidine Aptamer No. 13 can be administered to patients with wAMD at a dose of up to 5 to 15 mg/eye using the formulation described above via a pre-filled syringe consisting of 50 µL for injection with a ½ inch 30-33 gauge needle. Aptamer No. 13 is administered every 2 to 6 months compared to Avastin® or Lucentis® which are administered monthly, Macugen® which is administered every 6 weeks, or Eyelea® which can be administered monthly or bimonthly (every two months).

Administration of aptamer No. 13 is anticipated to improve or maintain the mean change in visual acuity (ETDRS letters) from baseline by 12 months of therapy comparable to existing antibody-based VEGF therapies, and is anticipated to be more efficacious than Macugen® because of the increased dose administered. Administration of aptamer No. 13 may be monitored for adverse events, including changes in ophthalmic examinations, intraocular pressure, fluorescein angiography, optical coherence tomography, ECG and laboratory variables. Further, given the longer duration of effect of aptamer No. 13 compared to other VEGF therapies, it is also anticipated that treatment with aptamer No. 13 can result in fewer side effects given the lower number of injections with a higher gauge needle over the treatment period.

Example 7. Treatment of Geographic Atrophy (GA) with HA-C5 Bispecific Aptamers

Aptamer No. 14 conjugated to 40 KDa PEG (ARC-1905, Zimura®) is an anti-complement C5 aptamer (Biesecker, G., L. Dihel, K. Enney, and R. A. Bendele, 1999, Immunopharmacology, 42:219-230) with demonstrated potent inhibition of complement activity and therapeutic effect in the treatment of GA. In this example, the aptamer component of Zimura® (aptamer No. 14) is tethered to aptamer No. 7 by solid phase synthesis to produce a bispecific aptamer consisting of an HA-binding domain and a C5 inhibitor domain to yield aptamer No. 15, which has a molecular weight of approximately 24,750 Da (Table 11). Alternatively, aptamer No. 7 is produced with a C6-disuflide linker, and is conju- Zimura® is presented as an isotonic, neutral pH formulation at a concentration of 30-40 mg/mL based on oligonucleotide molecular weight and is administered intravitreally at a 50-75 µL volume for a maximum dose of 2.0 mg/eye. The maximum dose of Zimura® is limited by the viscosity of the drug product solution. By contrast, in one embodiment, aptamer No. 15 is presented at a concentration of 100 mg/ml in a prefilled syringe administrable via a 27-33 gauge needle for a dose of 5 mg in a 50 µL volume of injection. The dynamic viscosity of a dosage form (or concentration) provided herein may be about 38,800 centipoise to about 194,100 centipoise, about 97,000 centipoise to about 485,500 centipoise, or about 194,100 centipoise to about 970,800 centipoise when formulated in a 50 µL pre-filled syringe with a ½ inch 27-gauge needle. The dynamic viscosity of a dosage form (or concentration) provided herein may be about 13,100 centipoise to about 65,000 centipoise, about 32,700 centipoise to about 164,000 centipoise, or about 65,000 centipoise to about 325,000 centipoise when formulated in a 50 µL pre-filled syringe with a ½ inch 30-gauge needle. Similarly, the dynamic viscosity of a dosage form (or concentration) provided herein may be about 2,800 centipoise to about 14,500 centipoise, about 7,300 centipoise to about 36,500 centipoise, or about 14,500 to about 75,000 centipoise when formulated in a 50 µL pre-filled syringe with a ½ inch 33 gauge needle.

In another embodiment, given the lower viscosity of aptamer No. 15 relative to Zimura®, it is anticipated that presentations of 200 to 250 mg/ml or greater would possess a sufficiently low viscosity to be administered in a 27-33 gauge needle to provide a dose of 10 to 15 mg or greater in a 50 µL volume of injection. In general, aptamers conjugated to an HA aptamer binding module may be formulated either in dilute phosphate buffer (for example, in the range of 5 to 10 mM phosphate) at or near pH 7.4, or in pure water adjusted to or near pH 7.4. Additives, including buffering salts, may be used sparingly, if at all, according to a recent publication from USP and the FDA.

The presentation of a therapeutic aptamer such as the aptamer No. 15 is anticipated to provide a favorable presentation for intravitreal administration compared to the same aptamer conjugated to a high molecular weight PEG, such as a branched 40 KDa PEG used for Macugen®, Fovista® and Zimura®. While conjugation of PEG to an aptamer confers the desired effect of extending intravitreal half-life, it also contributes substantially to the viscosity of the solution. PEG is a well-known shear thickener, meaning that the viscosity of a solution of given concentration is not a fixed parameter, but increases with increased shear force applied to the solution. This phenomenon leads to serious limitations in the administration of PEGylated aptamers because a compromise must be achieved between concentration of dosing solution and the diameter of the needle used to administer the drug. Conjugation of a therapeutic aptamer to an HA aptamer (HA-therapeutic aptamer bispecifics) presents the opportunity to achieve the requisite clinical concentration of drug product without encountering shear thickening. In addition, the lower overall size and molecular weight of the HA-therapeutic aptamer bispecific is only about 40% of the aptamer conjugated to a 40-kilodalton PEG. Thus, an HA-therapeutic aptamer bispecific is anticipated to be a more compact structure than the comparable PEGylated aptamer, leading to less intermolecular interaction. HA-therapeutic aptamer bispecific clinical products are more likely to achieve the requisite clinical concentration at a viscosity that permits administration via a needle of gauge 28, 30, or even 33. Thus, discomfort to the patient is minimized as is the risk of serious injury during administration.

Aptamer No. 15 can be administered to patients with GA at a dose of 5 to 15 mg/eye using the formulation described above via a pre-filled syringe consisting of 50 μL for injection with a ½ inch 30-33 gauge needle. Aptamer No. 15 may be administered alone or in combination with anti-VEGF therapy, which may consist of either 1.25 mg of Avastin®, 0.5 mg of Lucentis® or 2 mg of Eylea®, the injections of which can be performed independently.

Aptamer No. 15 is anticipated to have a half-life of 10 to 28 days to support administration every 3 to 6 months, whereas anti-VEGF therapy can be administered every 1 or 2 months based on the package insert for the selected anti-VEGF therapy.

Administration of aptamer No. 15 alone or in combination with anti-VEGF therapy is anticipated to improve the mean change in visual acuity (ETDRS letters) from baseline by 12 months of therapy, improve best corrected visual acuity, decrease drusen volume and retinal thickening as measured by OCT. Administration of aptamer No. 15 alone or in combination with anti-VEGF therapy may be monitored for adverse events, including changes in ophthalmic examinations, intraocular pressure, fluorescein angiography, optical coherence tomography, ECG and laboratory variables. Overall, the use of aptamer No. 15 alone or in combination with anti-VEGF therapy is anticipated to be more efficacious than Zimura® alone or combination with anti-VEGF therapy because of the increased dose of anti-C5 therapeutic administered. Further, given the longer duration of effect of aptamer No. 15 compared to Zimura®, it is also anticipated that treatment with aptamer No. 15 can result in fewer side effects given the lower number of injections with a higher gauge needle over the treatment period.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A composition comprising a therapeutic aptamer conjugated to a vitreous component binding moiety, wherein said vitreous component binding moiety comprises an aptamer that selectively binds to hyaluronan.

2. The composition of claim 1, wherein said aptamer that selectively binds to hyaluronan is an RNA aptamer or a modified RNA aptamer.

3. The composition of claim 1, wherein said aptamer that selectively binds to hyaluronan is a DNA aptamer or a modified DNA aptamer.

4. The composition of claim 1, wherein said aptamer selectively binds to hyaluronan with a $K_d$ of less than 1 mM.

5. The composition of claim 1, wherein said composition has an intravitreal half-life of at least 6 days in a human, an intravitreal half-life of at least 2 days in a rabbit, an intravitreal half-life of at least 3 days in a non-human primate, or any combination thereof.

6. The composition of claim 1, wherein said therapeutic aptamer is a therapeutic aptamer for treatment of a retinal disease.

7. The composition of claim 6, wherein said retinal disease is selected from the group consisting of: macular degeneration, geographic atrophy, diabetic macular edema, diabetic retinopathy, retinal vein occlusion, Stargardt disease, retinal neovascularization, and uveitis.

8. The composition of claim 1, wherein said therapeutic aptamer is an inhibitor of hypoxia-inducible factor-1α, vascular endothelial growth factor, platelet-derived growth factor, angiopoietin-2, interleukin-6, interleukin-2, interleukin-8, complement Factor D, complement Factor P, complement component 5, complement component 3, integrin, or any combination thereof.

9. The composition of claim 1, wherein: (i) said vitreous component binding moiety comprises an aptamer that selectively binds to hyaluronan with a $K_d$ of less than 1 mM; (ii) said composition has an intravitreal half-life of at least 6 days in a human, an intravitreal half-life of at least 2 days in a rabbit, an intravitreal half-life of at least 3 days in a non-human primate, or any combination thereof; and (iii) said therapeutic aptamer is a therapeutic aptamer for treatment of macular degeneration.

10. The composition of claim 1, wherein said composition does not comprise a polyethylene glycol polymer of molecular weight greater than 30 kDa.

11. The composition of claim 1, wherein said therapeutic aptamer is capable of dissociating from said vitreous component binding moiety over a period of time.

12. The composition of claim 1, wherein said composition has a molecular weight of less than 40 kDa and an intravitreal retention time comparable to that of a composition comprising a 40 kDa polyethylene glycol polymer.

13. The composition of claim 12, wherein said composition has a viscosity that is no more than half of a viscosity of a composition comprising a 40 kDa polyethylene glycol polymer, when said compositions are each formulated in a liquid formulation suitable for intravitreal administration.

14. The composition of claim 1, wherein said composition is formulated in a liquid formulation.

15. The composition of claim 14, wherein said composition is present in said liquid formulation at a concentration of at least 40 mg/ml when said liquid formulation is formulated for intravitreal administration.

16. The composition of claim 15, wherein said liquid formulation has a dynamic viscosity of less than 970,800 centipoise when formulated in a 50 µL volume and administered with a ½ inch 27-gauge needle.

17. The composition of claim 15, wherein said liquid formulation has a dynamic viscosity of less than 325,000 centipoise when formulated in a 50 µL volume and administered with a ½ inch 30-gauge needle.

18. The composition of claim 15, wherein said liquid formulation has a dynamic viscosity of less than 75,000 centipoise when formulated in a 50 µL volume and administered with a ½ inch 33-gauge needle.

19. A method of treating a retinal disease in a subject in need thereof, the method comprising: administering to said subject in need thereof a therapeutically effective amount of a composition of claim 1, thereby treating said retinal disease.

20. The method of claim 19, wherein said administering comprises administering said composition to said subject by intravitreal administration.

21. The method of claim 19, wherein said administering comprises administering said composition at least once every 8 weeks.

22. The method of claim 19, wherein said administering said composition comprises administering said composition using a needle with a gauge within a range of 27 gauge to 33 gauge.

23. The method of claim 22, wherein said needle within a range of 27 gauge to 33 gauge has a length of ½-inch or less.

24. The method of claim 19, wherein said administering comprises administering a dose of said composition of at least 2 mg to said subject in a single intravitreal administration.

25. The method of claim 19, wherein said therapeutically effective amount is from 0.1 mg to 50 mg in 15 µl to 100 µl per eye.

26. The composition of claim 1, wherein said therapeutic aptamer is an RNA aptamer or a modified RNA aptamer.

27. The composition of claim 1, wherein said therapeutic aptamer is a DNA aptamer or a modified DNA aptamer.

28. The method of claim 19, wherein said retinal disease is selected from the group consisting of: macular degeneration, geographic atrophy, diabetic macular edema, diabetic retinopathy, retinal vein occlusion, Stargardt disease, retinal neovascularization, and uveitis.

* * * * *